United States Patent [19]
Backman et al.

[11] Patent Number: 5,196,350
[45] Date of Patent: Mar. 23, 1993

[54] LIGAND ASSAY USING INTERFERENCE MODULATION

[75] Inventors: Keith C. Backman, Bedford; Christiane Munkholm, Salem, both of Mass.

[73] Assignee: OmniGene, Inc., Cambridge, Mass.

[21] Appl. No.: 706,772

[22] Filed: May 29, 1991

[51] Int. Cl.$^5$ .................. C12Q 1/00; G01N 33/53; G01N 33/566; G01N 33/554
[52] U.S. Cl. .................. 436/501; 435/7.1; 435/7.92; 435/7.93; 435/7.94; 435/7.95; 436/518; 436/524
[58] Field of Search .......... 435/7.1, 7.92, 7.93, 435/7.94, 7.95; 436/501, 518, 524

[56] References Cited
U.S. PATENT DOCUMENTS

| | | |
|---|---|---|
| 4,313,734 | 2/1982 | Leuvering . |
| 4,407,964 | 10/1980 | Elings et al. . |
| 4,421,860 | 10/1981 | Elings et al. . |
| 4,487,839 | 12/1984 | Kamentsky . |
| 4,521,522 | 6/1985 | Lundstrom et al. . |
| 4,537,861 | 8/1985 | Elings et al. . |
| 4,647,544 | 3/1987 | Nicoli et al. . |
| 4,759,628 | 7/1988 | Tatsuno et al. . |
| 4,876,208 | 10/1989 | Gustafson et al. . |

OTHER PUBLICATIONS

Aktins, (1976), Physics, John Wiley & Sons, N.Y., pp. 424-437.
Karp, (1979), Cell Biology, McGraw-Hill Inc., N.Y., pp. 49-54.
Bhatia et al., (1989), Analytical Biochem., 178:408-413.
Cullen, D. et al., *Biosensors*, 3, (4):211-225 (1987).
Born, M. et al., *Principles of Optics*, Pergamon Press, Elmsford, New York (6th Ed., 1983).
Cobble, J. A., "Picosecond Coherence Time Measurement with a Double Slit", *Applied Optics*, 26(19):4048-4051 (Oct. 1, 1987).

Primary Examiner—Christine M. Nucker
Assistant Examiner—D. R. Preston
Attorney, Agent, or Firm—Hamilton, Brook, Smith & Reynolds

[57] ABSTRACT

An optical detection method for detecting specific ligands in an immunoassay is formed by diffracting a beam of light through slits formed in a mask and thererby forming an interference pattern. The diffracted light of one of the slits is distributed by an assay having a ligand which when reacted with anti-ligand changes the optical characteristics of the assay thereby changing the interference pattern in a concentration dependent manner.

22 Claims, 11 Drawing Sheets

CHEMICAL

Analyte capture on assay slide

Au-antibody capture

Silver precipitation

OPTICAL

Fig. 4d $\quad S_2 < S_1 \quad$ Loss of transparency, $S_2$

Fig. 4e $\quad I_2 < I_1 \quad$ Loss of transmission, $I_2$

Fringe modulation from $I_2$ decreases

Fig. 4g $\quad \Delta V \propto \Delta \text{conc.} \quad$ Relate change in fringe to concentration analyte

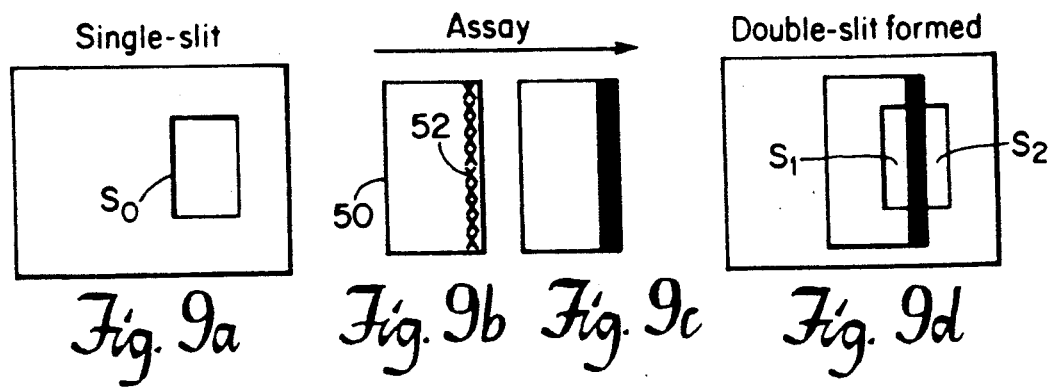
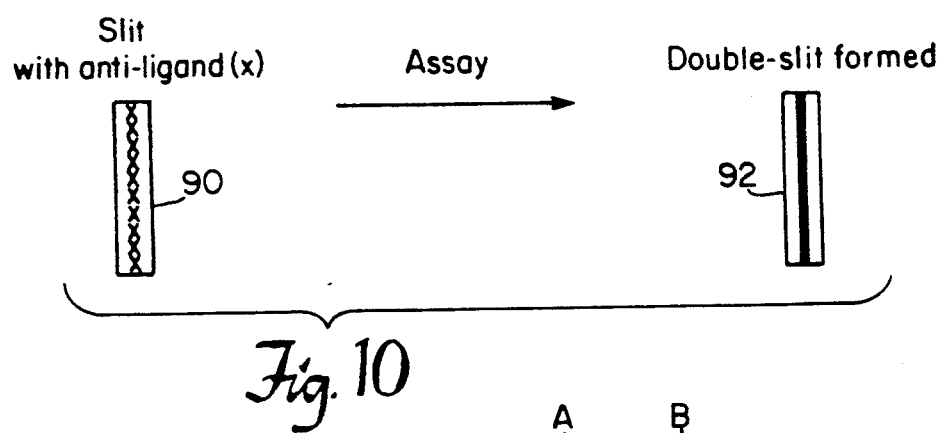
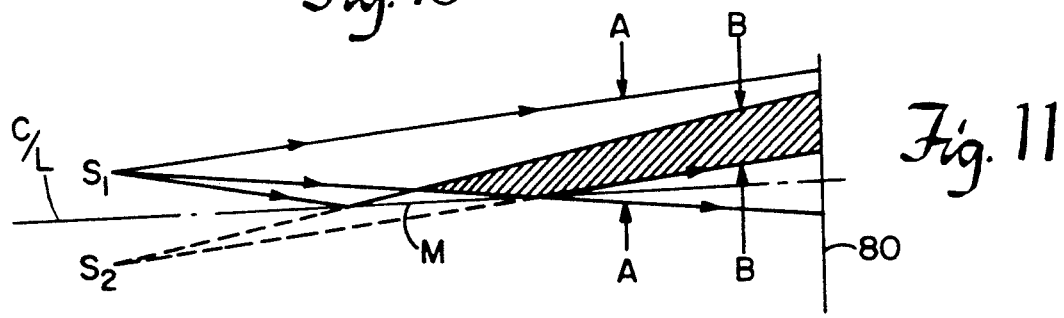
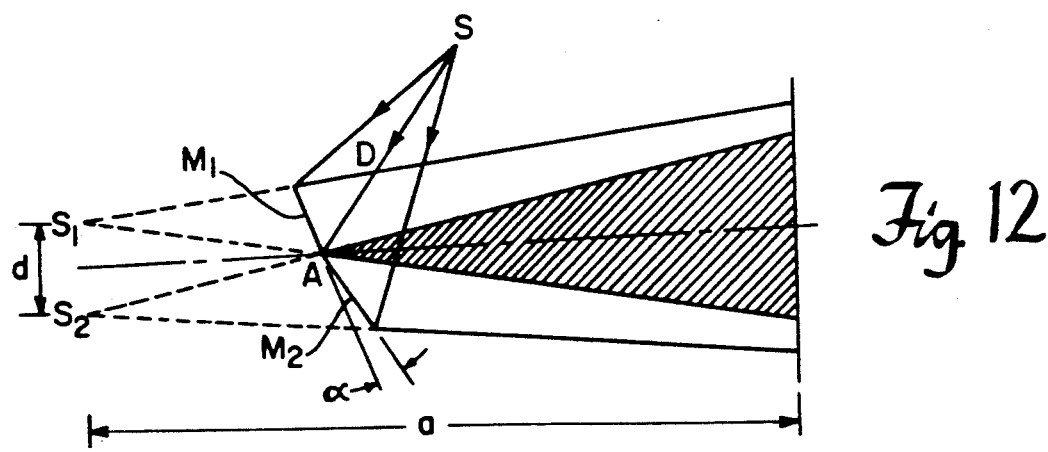

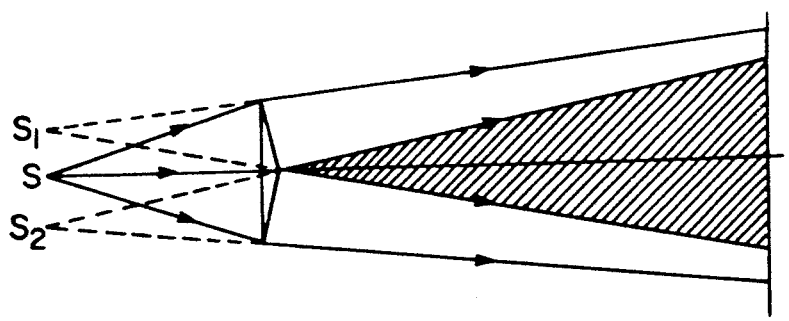
Fig. 13
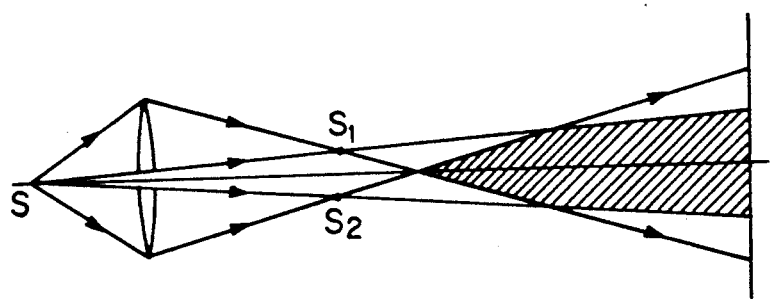
Fig. 14
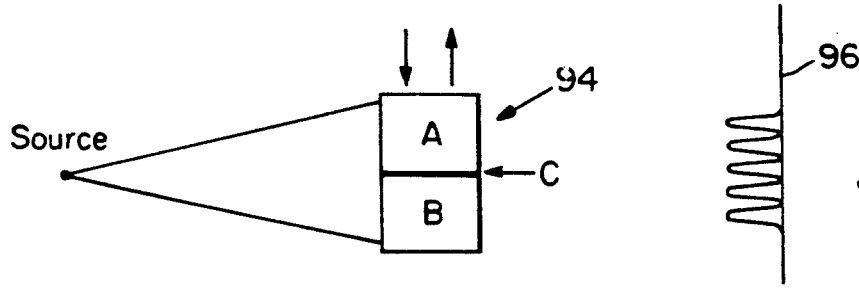
Fig. 15
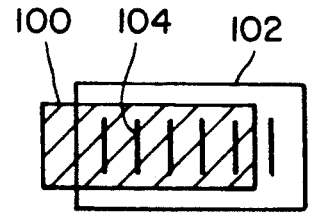
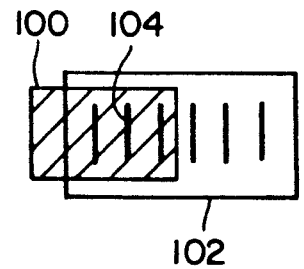
Fig. 17
Fig. 18
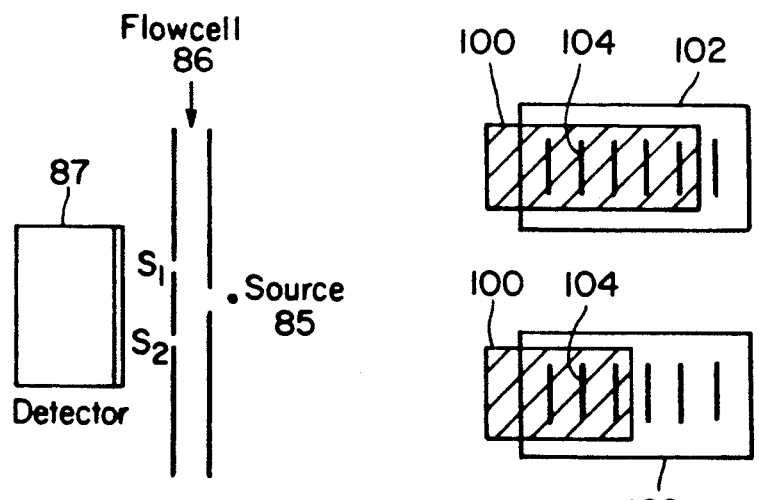
Fig. 16

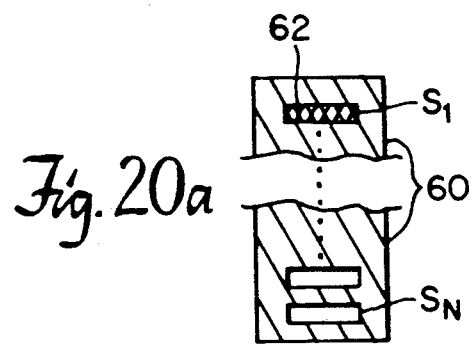 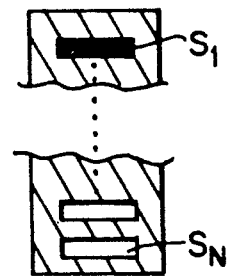
*Fig. 20a*  *Fig. 20b*
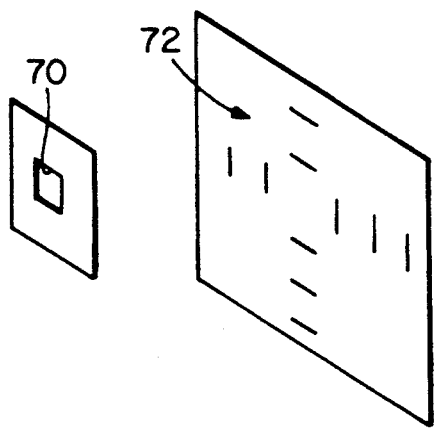 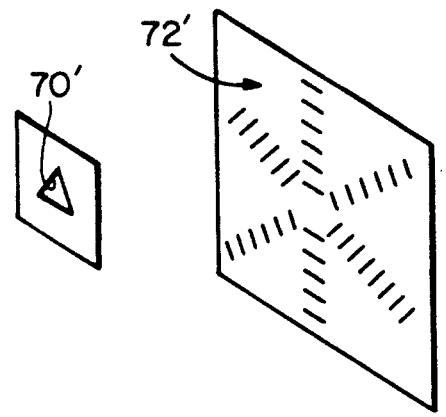
*Fig. 21a*  *Fig. 21b*
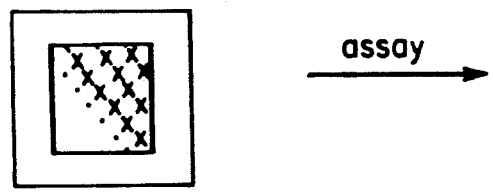 
*Fig. 21c*  *Fig. 21d*

LIGAND ASSAY USING INTERFERENCE MODULATION

BACKGROUND OF THE INVENTION

It is desirable in certain circumstances to measure very low concentrations of certain organic compounds. In medicine, for example, it is very useful to determine the concentration of a given kind of molecule, usually in solution, which either exists naturally in physiological fluids (e.g. blood or urine) or which has been introduced into the living system (e.g. drugs or contaminants). Because of the rapidly advancing state of understanding of the molecular basis of both the normal and diseased states of living systems, there is an increasing need for methods of detection which are quantitative, specific to the molecule of interest, highly sensitive and relatively simple to implement. Examples of molecules of interest in a medical and/or biological context include, but are not limited to, drugs, sex and adrenal hormones, biologically active peptides, circulating hormones and antigens associated with tumors or infectious agents. In the case of drugs, for example, the safe and efficacious use of a particular drug requires that its concentration in the circulatory system be held to within relatively narrow bounds, referred to as the therapeutic range.

One broad approach used to detect the presence of a particular compound, referred to as the analyte, is the immunoassay, in which detection of a given molecular species, referred to generally as the ligand, is accomplished through the use of a second molecular species, often called the antiligand, or the receptor, which specifically binds to the first compound of interest. The presence of the ligand of interest is detected by measuring, or inferring, either directly or indirectly, the extent of binding of ligand to antiligand. The ligand may be either monoepitopic or poly epitopic and is generally defined to be any organic molecule for which there exists another molecule (i.e. the antiligand) which specifically bonds to said ligand, owing to the recognition of some portion of said ligand. Examples of ligands include macromolecular antigens and haptens (e.g. drugs). The antiligand, or receptor, is usually an antibody, which either exists naturally or can be prepared artificially. The ligand and antiligand together form a homologous pair. Throughout the text the terms antigen and antibody, which represent typical examples, are used interchangeably with the terms ligand and antiligand, respectively, but such usage does not signify any loss of generality. In some cases, the antibody would be the ligand and the antigen the antiligand, if the presence of the antibody is to be detected.

Implementation of a successful immunoassay requires a detectable signal which is related to the extent of antigen-antibody binding which occurs upon the reaction of the analyte with various assay reagents. Usually that signal is provided for by a label which is conjugated to either the ligand or the antiligand, depending on the mode of operation of the immunoassay. Any label which provides a stable, conveniently detectable signal is an acceptable candidate. Physical or chemical effects which produce detectable signals, and for which suitable labels exist, include radioactivity, fluorescence, chemiluminescence, phosphorescence and enzymatic activity, to name a few.

Broadly speaking, immunoassays fall into two general categories—heterogeneous and homogeneous. In heterogeneous assays, the purpose of the label is simply to establish the location of the molecule to which it conjugates—i.e. to establish whether the labeled molecule is free in solution or is part of a bound complex. Heterogeneous assays generally function by explicitly separating bound antigen-antibody complexes from the remaining free antigen and/or antibody. A method which is frequently employed consists of attaching one of the members of the homologous pair to a solid surface by covalent binding, physical absorption, or some other means. When antigen-antibody binding occurs, the resulting bound complexes remain attached to this solid surface (composed of any suitable inert material such as plastic, paper, glass, metal, polymer gel, etc.), allowing for separation of free antigen and/or antibody in the surrounding solution by a wash step. A variation on this method consists of using small (typically 0.05 to 20 microns) suspendable particles to provide the solid surface onto which either antigen or antibody is immobilized. Separation is effected by centrifugation of the solution of sample, reagents and suspendable beads at an appropriate speed, resulting in selective sedimentation of the support particles together with the bound complexes.

In the homogeneous assay, the signal obtained from the labeled ligand or antiligand is modified, or modulated, in some systematic, recognizable way when ligand-antiligand binding occurs. Consequently, separation of the labeled bound complexes from the free labeled molecules is no longer required.

There exist a number of ways in which immunoassays can be carried out.

In the competitive mode, the analyte, assumed to be antigen, is allowed to compete with a known concentration of labeled antigen (provided in reagent form in the assay kit) for binding to a limited number of antibody molecules which are attached to a solid matrix. Following an appropriate incubation period, the reacting solution is washed away, ideally leaving just labeled antigen-antibody complexes attached to the binding surface, thereby permitting the signal from the labels to be quantitated.

In another method, called the sandwich mode, the analyte, again assumed to be antigen, reacts with an excess of surface-immobilized antibody molecules. After a suitable incubation period, an excess of label-conjugated antibody is added to the system to react with another bonding site on the antigen. After this reaction has gone to essential completion, a wash step removes unbound labeled antibody and other sources of contamination, permitting measurement of the signal produced by labels which are attached to antibody-antigen-antibody complexes. Any non-specific bonding of the labeled antibody to the surface will, however, contribute to the signal.

In yet another approach, called the indirect mode, the analyte, this time assumed to consist of specific antibody, is allowed to bind to surface-immobilized antigen which is in excess. The binding surface is then washed and allowed to react with label-conjugated antibody. After a suitable incubation period the surface is washed again, removing free labeled antibody and permitting measurement of the signal due to bound labeled antibody. The resulting signal strength varies inversely with the concentration of the starting (unknown) antibody, since labeled antibody can bind only to those immobilized antigen molecules which have not already complexed to the analyte.

One of the most sensitive immunoassays developed thusfar is the radioimmunoassay (RIA), in which the label is a radionuclide, such as $I^{125}$, conjugated to either member of the homologous (binding) pair.

Fluorescence provides a potentially attractive alternative to radioactivity as a suitable label for immunoassays. For example, fluorescein (usually in the form of fluorescein isothiocyanate, or "FITC") and a variety of other fluorescent dye molecules can be attached to most ligands and receptors without significantly impairing their binding properties. Fluorescent molecules have the property that they absorb light over a certain range of wavelengths and (after a delay ranging form $10^{-9}$ to $10^{-4}$ seconds) emit light over a range of longer wavelengths. Hence, through the use of a suitable light source, detector and optics, including excitation and emission filters, the fluorescence intensity originating from labeled molecules can be determined.

Use of an enzyme as a label has produced a variety of useful enzyme immunoassays (EIA), the most popular of which is known as ELISA. In the typical heterogeneous format a sandwich-type reaction is employed, in which the ligand of interest, assumed here to be antigen, binds to surface-immobilized specific antibody and then to an enzyme-antibody conjugate. After suitable incubation, any remaining free enzyme conjugate is eliminated by a wash or centrifugation step. A suitable substrate for the enzyme is then brought into contact with the surface containing the bound complexes. The enzyme-substrate pair is chosen to provide a reaction product which yields a readily detectable signal, such as a color change or a fluorescence emission. The use of an enzyme as a label serves to effectively amplify the contribution of a single labeled bound complex to the measured signal, because many substrate molecules can be converted by a single enzyme molecule.

As may be seen from the above background summary many of the immunoassay techniques rely on optical methods to detect specific ligands in a sample matrix and it may be said that these techniques have fallen generally into three optical classes:

1) Methods based on the molecular absorbance of light, which comprise all standard spectroscopic methods such as absorbance, fluorescence, phosphorescence, fluorescence polarization, circular dichroism, Raman, and infrared spectroscopies;

2) Methods based on the generation of light by a chemical reaction, which is known as chemiluminescence, or bioluminescence when the reaction is catalyzed by an enzyme; and 3) Methods based on the change in the direction of propagation of a lightwave such as refractometry, optical rotary dispersion, and methods based on the scattering of light.

With all of the above the signal is collected and measured by a detection apparatus which monitors the phenomenon as it occurs within the sample's molecular population. The measurement is a function of the intensity or degree of change occurring within the sample. Although most of these methods produce isotropic signals, even the anisotropic methods such as fluorescence polarization, produce signals which are fundamentally measured as intensities.

Emerging now are optical detection techniques which may comprise a new and fourth class of optical methods based on spatial patterns produced by the interaction of radiation with the ligand or anti-ligand. In this class of optical detection techniques the optical signal is collected outside of the sample, as a pattern or an intensity measured at more than one geometrically defined spatial position. The following descriptions are representative of this new class of optical detection methods.

Nicoli in U.S. Pat. No. 4,647,544 issued Mar. 3, 1987 entitled "Immunoassay Using Optical Interference Detection" describes optical detection of a binding reaction between a ligand and an antiligand wherein a pattern is formed on a substrate by a spatial array of microscopic dimensions of antiligand material immobilized to a substrate. Upon exposure to the sample the ligand binds to the substrate to form a physical pattern. A source of optical radiation is directed to the pattern at a particular incidence angle to produce an optical interference pattern in accordance with the binding reaction and with a strong scattering intensity at one or more Bragg scattering angles. An optical detector is located relative to the pattern and aligned with the Bragg scattering angle to detect the strong scattering intensity and produce a signal representative of the binding reaction.

Another patent, "Diffraction Immunoassay and Reagents" EPO 0276968 published Aug. 3, 1988 describes a "biograting" based assay in which a biological diffraction grating consisting of lines of active binding reagent is formed on a silicon substrate surface. After contacting the assay surface with the sample and separating the sample from the assay, the surface is illuminated and the binding of analyte to surface in a uniform manner generates a diffraction pattern. An optical detector, or array of detectors, positioned at predetermined angles is used to measure the diffracted light.

PCT Application No. PCT/GB85/00427 describes the use of fluorescently tagged molecules binding to a substrate pattern so that the fluorescence emission is organized into a narrow cone of angles instead of being uniform in all directions.

In each of these examples the detected signal is produced by light interacting with analytes that have been entrapped on a surface in a geometric manner, and the detectable signal is characterized by both amplitude and pattern formation.

These spatial based optical detection immunoassay methods are controlled by the spatial geometry, formed by either the ligand or antiligand, which must be of extremely fine detail and small dimensions; sophisticated immobilization technology will be required which may be difficult to reproducibly implement for many useful ligands or antiligands.

SUMMARY OF THE INVENTION

The invention comprises a method of modulating an interference pattern created by interference between two or more light beams by reacting a ligand with an antiligand in an assay to cause a change in the optical characteristics of the assay. This change in optical characteristics is used to disturb the interference pattern by placing the reacted assay in the path of one or more of the light beams creating the interference pattern. The resultant change in the interference pattern is dependent on the concentration of the ligand and can be used to detect the presence of the ligand and its concentration in the assay.

In a first embodiment, an interference pattern is formed by projecting light through a mask having at least two narrow parallel slits, having a width which can be very small but remains larger than the wavelength of the source light, and separated by a distance which exceeds the slit width. The light is thereby diffracted into two or more light beams which interfere and form an interference pattern, which may, for example, be visualized by projection on a screen. One or more of the slits may then be blocked to produce a different interference pattern. An assay surface with a ligand which when reacted with an anti-ligand reduces the transparency of the assay surface is then placed on or over a slit or slits, causing the interference pattern to change to a pattern which is intermediate between the standard pattern formed by the uncovered multi-slit and the standard pattern formed when the slit or slits relevant to the assay surface are completely obscured. The change in the interference pattern compared to the standard is measured and related to the concentration of the assay ligand.

Preferably a source of monochromatic light, such as a laser, is used to project light through multi-slit openings formed on a foil mask. An assay slide is mounted adjacent to the foil to obstruct one or more slits.

A lens may be used to magnify the interference pattern so that is can be projected onto a screen and photographed. The resultant photographs are then analyzed by a densitometer to determine the intensity of the light at certain points on the pattern before and after the slit is covered, thereby to determine the presence of he ligand and its concentration in the assay.

Alternatively, the intensity of the pattern can be analyzed in real time using an array of pixels formed by photodetectors to form electrical signals corresponding to each pixel and processing these signals in a computer.

BRIEF DESCRIPTION OF THE DRAWINGS

FIG. 7(a) is a plot of the visibility $V_2$ of the fringe pattern as a function of the percent of transmission ($I_2\%$) through the second slit $S_2$.

FIGS. 9a-9d is a schematic flow diagram of an alternate embodiment of the invention.

FIG. 10 is a schematic of yet another alternate embodiment.

FIG. 11 is a schematic of an alternate embodiment in which the double-slit pattern is produced by a virtual slit $S_2$ and an actual slit $S_1$ and a mirror M.

FIG. 12 is a schematic of a Fresnel's mirror embodiment of the invention.

FIG. 13 is a schematic of a bi-prism embodiment of the invention.

FIG. 14 is a schematic of a Billet's split lens embodiment of the invention.

FIG. 15 is a schematic of a flow cell embodiment.

FIG. 16 is a schematic of an alternate flow cell embodiment.

FIG. 17 is a schematic illustrating an alternate embodiment wherein N slits are formed and N-X slits covered by the assay and wherein N=6 and X=5.

FIG. 18 is the same as FIG. 17 except that N=6 and X=3.

FIG. 20(a) is a schematic drawing of an alternate embodiment of a two or more slit embodiment in which the assay substrate is formed with slits.

FIG. 20(b) is a schematic as in FIG. 20(a) showing that the reaction causes slit S1 to become less transparent.

FIG. 21(a) is an alternate embodiment in which the slitopening is replaced by a square opening.

FIG. 21(b) is a schematic drawing of an alternate embodiment of FIG. 20(a) wherein the slit opening is triangular in shape.

FIG. 21(c) is a schematic which illustrates formation of an assay on a diagonal half of a square slit to form a triangular based diffraction pattern.

FIG. 21(d) is a schematic as in FIG. 21(c) showing the formation of the triangular pattern.

DESCRIPTION OF THE EMBODIMENT

A. Background Theory

Figure 1:
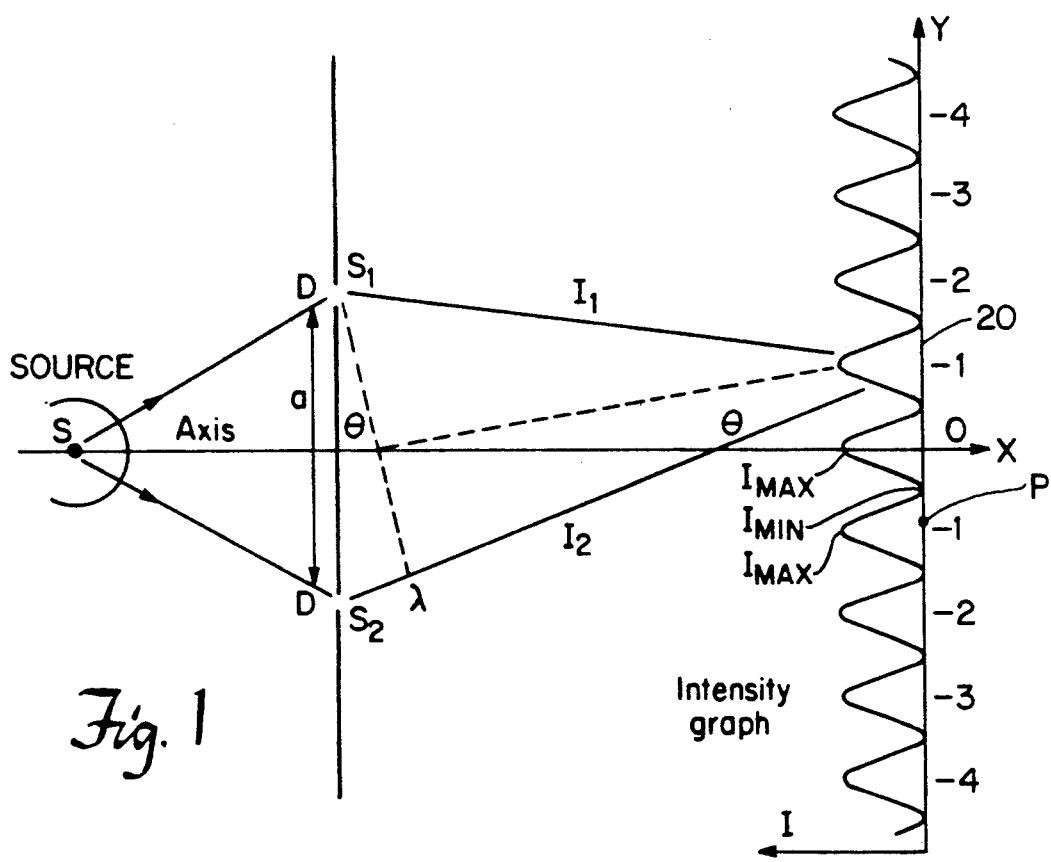
FIG. 1 is a diagram of light interference produced by a two-slit mask to illustrate the theory behind the invention.

In 1801 Thomas Young demonstrated the phenomenon of interference bands produced by a light shining through two identical and closely spaced slits. A diagram of the optical configuration used by Young is shown in FIG. 1. A light source (S) is incident on two narrow, parallel slits ($S_1$ and $S_2$). Each slit has a width (D) which can be very small but remain larger than the wavelength of light. The slits are separated by a distance (a), which exceeds D. The light passing through the slits is diffracted and emerges as two wavefronts with identical wavelength and phase. The two wavefronts interfere and produce a visible interference pattern on the screen 20. The pattern consists of a series of bright and dark parallel bands which are typically referred to as fringes.

The overall light amplitude at any given point in the interference pattern is the result of the superposition of the two wave amplitudes from $S_1$ and $S_2$. Two waves that add constructively produce a bright fringe (maxima) while two waves that add destructively produce a dark fringe (minima). The distance between two adjacent maxima is calculated by:

$$Y = \frac{m \times \lambda}{a} \qquad \text{Eq. (1)}$$

where X is the distance from the slits to the screen, $\lambda$ is the wavelength of the light, and m is an integer used to designate the position of the fringe. The central fringe, located on the symmetry axis, is called the zero-order maximum. The first maximum on either side ($m = \pm 1$), is called the first-order maximum, and the maxima continue in either direction, through the higher orders. The minima are located exactly halfway between the maxima and are completely dark only when the two slits provide equal intensities.

When working with Eq. 1 the quantities X and a are both controlled by the experimental design and the value for Y can be measured from the fringe pattern, leaving only as an unknown value. Thus, one can use this equation to determine the wavelength of light, which was another historical achievement of the original double-slit experiment.

Figure 2:
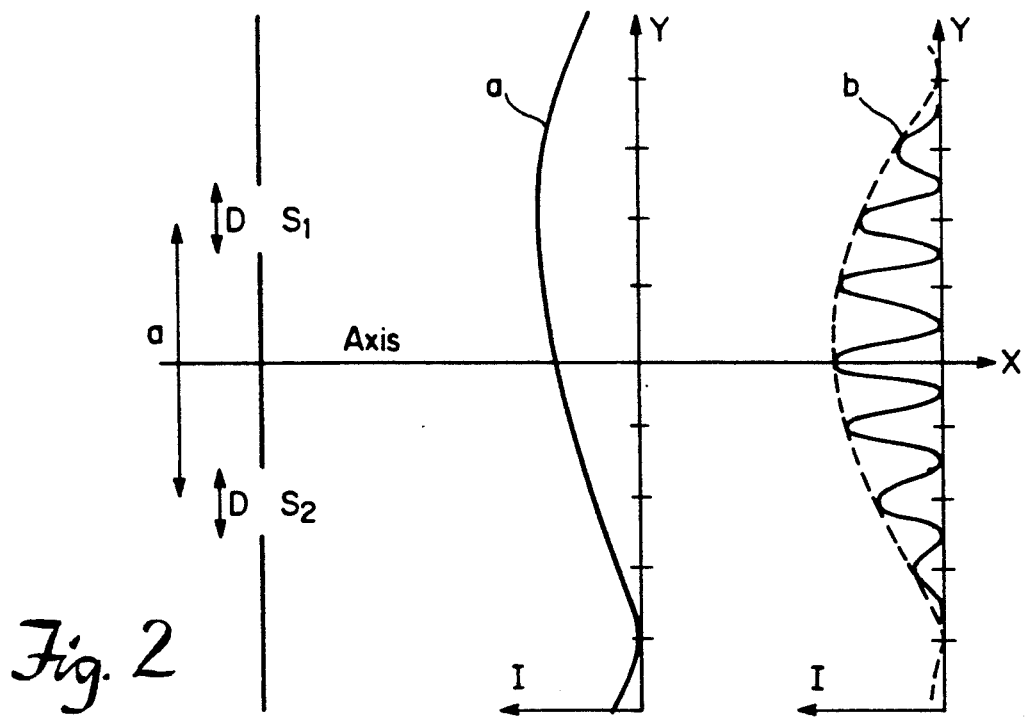
FIG. 2 is a diagram illustrating in curve (a) the diffraction pattern when only one slit ($S_1$) is open and in curve (b) the interference pattern when both slits ($S_1$ & $S_2$) are open.

When only one of the two slits is open a broad central diffraction peak is obtained centered on the open slit as shown in FIG. 2, curve a. With two slits open, the overlapping wavefronts of the diffraction bands produced by the individual slits combine to form an interference pattern located within the boundaries of the diffraction bands; the interference fringes are visible where each of the diffraction bands would have been observed.

B. Principle of Assay Based on Double-Slit Interference Pattern

The assay of the invention is based on a transduction mechanism of double-slit or multi-slit interference modulation. As stated previously, complete loss of transmission through only one slit in a double-slit interference configuration will produce a collapse of the fringe pattern to the single-slit diffraction band. A partial loss of transmission produces an intermediate pattern where the amplitudes of the interference maxima and minima are moving towards the condition of the diffraction band envelope. Therefore, any method of reducing the transparency of a slit can be related to a loss of fringe pattern.

One way to convert this process to an assay is to provide a chemistry which produces a localized coverage over one slit which is opaque enough to reduce the transmission of light through the slit. The reduction of light through the slit decreases the intensity of light available for interference with light emanating from the other slit, and thus decreases the formation of the resulting fringe pattern. In practice, the surface coverage due to the assay is equated with a predictable change of fringe pattern.

The chemistry for producing loss of transmission through a slit can involve the temporary or permanent localization on the surface of the slit of any optically dense molecule or material which will cause a scattering or absorbance of the incident radiation from a source. Any physical phenomena that can alter or attenuate radiation transmission can affect the interference fringe formation. Therefore, any chemical phenomena producing one or more of these physical phenomena can potentially be assayed by this technology. The physical phenomena may comprise a change in reflectance, absorbance, phase, refraction, or polarization of light impinging on an assay. Items capable of behaving thusly include colloidal gold-labeled molecules, colorimetric labels and pigments, bacteria, polymeric particles, cells, Langmuir-Blodgett films, as well as other polymeric films.

For loss of transmission by means of light absorbance, materials must be used that absorb at the frequency of the incident light. Table 1 below lists the spectral color and associated wavelengths of a variety of colored compounds. For example, using a HeNe laser which emits a light of wavelength 630 nm, one would predict that blue/blue-green materials would absorb the energy. If one wanted to detect, for example, a yellow compound then the laser source would be changed to one working in the 430 nm range.

An absorbance-modulated interference system may also be used to detect multiple analytes in a sample with a variable, incoherent source, such as a Xenon arc lamp and a scanning monochromater. As a scanning spectrophotometer measures an absorbance spectrum as a function of the frequency of the incident radiation it may also be possible to measure the interference patterns produced by the transmissions at different frequencies. In this way, one could analyze a sample containing a variety of molecules with non-overlapping absorbance spectra; at a radiation wavelength coinciding with the absorbance maximum of a particular molecule in the sample the decrease of the interference pattern would be due to the attenuation resulting from the concentration of the molecule. Each molecule in the sample would cause attenuation of transmission at a discrete wavelength, and in this way multiple analytes could be detected in the region of a single slit ($S_2$).

TABLE 1

COLORS OF COMPOUNDS, SPECTRAL COLORS AND WAVELENGTHS

| Color of Compound | Spectral color absorbed | Approx. wavelength (nm) |
|---|---|---|
| Colorless | Ultraviolet | <400 |
| Lemon Yellow | Violet | 410 |
| Yellow | Indigo | 430 |
| Orange | Blue | 480 |
| Red | Blue-green | 500 |
| Purple | Green | 530 |
| Violet | Lemon yellow | 560 |
| Indigo | Yellow | 580 |
| Blue | Orange | 610 |
| Blue-green | Red | 680 |
| Green | Purple-red | 720 |
| Colorless | Infrared | >720 |

C. Preferred Embodiment of Apparatus of the Invention

Figure 3:
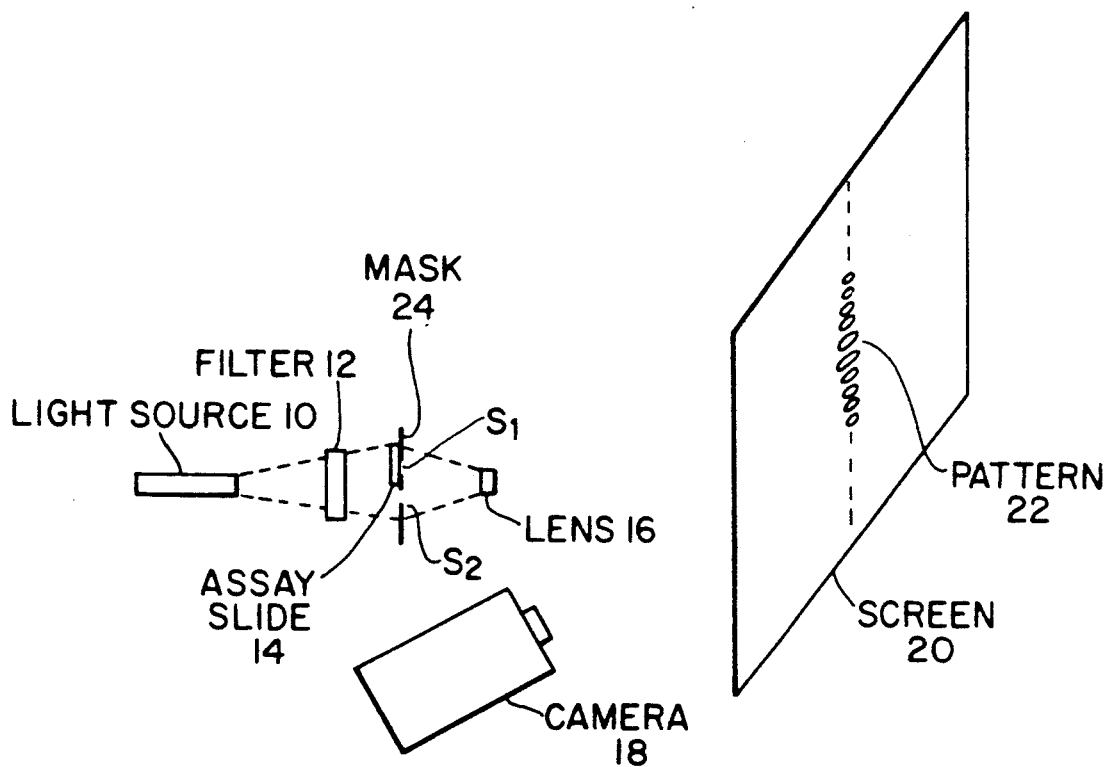
FIG. 3 is a schematic diagram of a preferred embodiment of the invention.

Turning now to FIG. 3 the apparatus for a first embodiment of the invention will be describe din connection therewith.

A light source 10 is disposed on a track (not shown) of an optical bench adjacent and in line with a foil mask 24 which is also mounted on the track. Mask 24 is formed with at least two narrow vertical slits $S_1$ and $S_2$. An assay is formed on assay slide 14 which is positioned on mask 24 so as to cover slit $S_1$.

An optional filter 12 is disposed on the track between source 10 and mask 24. If source 10 is a laser emitting highly intense monochromatic light, filter 12 may be a neutral density filter used to adjust the intensity of the light. If source 10 is a broad band moderately intense light source, filter 12 may be used to filter all but the desired wavelength for projection on the mask 24.

Light passing through the slits $S_1$ and $S_2$ is diffracted and the resulting wavefronts of diffracted light interfere to create a fringe pattern 22 which is magnified by lens 16 and projected onto screen 20. Note: Optionally, a second lens (not shown) may be disposed on the side of the mask nearest the source to increase the distribution of the pattern at the origin O. Camera 18 is used to photographically record the image of the pattern. This image may then be processed by converting the fringe patterns to intensity graphs using a densitometer and analyzing the intensity graphs produced with and without the slit covered by the assay to determine the concentration of the ligand in the assay.

The double-slit mask component 24 is a critical item in this process and must be of high quality. Preferably the mask is cut out of foil by a laser process. Three different sizes have been experimented with as shown in Table 2 below. Those skilled in the art will appreciate that the dimensions indicated have been arbitrarily selected from a continuum of suitable values, and are exemplary rather than limiting on the invention.

TABLE 2

| | DIMENSIONS OF AIR SLITS | | |
|---|---|---|---|
| Foil # | Slit width ($\mu$m) | Slit separ. ($\mu$m) | Slit length (mm) |
| 1 | 100 | 500 | 10 |
| 2 | 50 | 500 | 2 |
| 3 | 50 | 1000 | 2 |

Foil #2 produces the most intense and distinct fringe patterns in the current format. The fringe separation (Y) for this foil when placed at X distance from a screen are determined from Eq. 1 and are listed in Table 3 below.

TABLE 3

| CALCULATED FRINGE SEPARATIONS FOR FOIL #2 AT VARYING DISTANCES BETWEEN SLITS AND SCREEN | | | |
|---|---|---|---|
| X (cm) | a ($\mu$m) | $\lambda$ ($\mu$m) | Y ($\mu$m) |
| 50 | 550 | 0.633 | 575.4 |
| 40 | 550 | 0.633 | 460.4 |
| 30 | 550 | 0.633 | 345.2 |
| 20 | 550 | 0.633 | 230.2 |
| 10 | 550 | 0.633 | 115.1 |
| 5 | 550 | 0.633 | 57.5 |

The foil mask is secured on a magnetic mount (not shown) which is then placed on a magnetic strip attached to an X-Y-Z positioned in line with the light source 10. The assay requires positioning of the assay slide over one slit and this must be done so that the slide edge remains between two slits and does not cause any diffraction of the light beam transmitting through the uncovered slit.

In an experimental model the light source comprised a HeNe laser (Uniphase, 2 mW), generating monochromatic light at 633 nm. Neutral density filters were used to reduce the laser intensity.

The fringe patterns were recorded on film (Polaroid film #667, 3000ASA) and subsequently converted to intensity graphs by a video densitometer (PFGplus 640-3-U-RT PCVision Plus Frame Grabber with a 640×480 Display, OPTIMAS - Optical Measurement & Analysis Software, PVM-1342Q Sony Trinatron 13" color monitor with multiple inputs, Logimouse Plus—Logitech Mechanical Mouse, SYS/386-80-color-1 IBM Compatible 386 20 Mhz with EGA Color Monitor and 80 Megabyte Hard Drive) using a video camera (815-2000-0000 Cohu Series 4800 High Resolution CCD Monochrome Camera) focused on the illuminated photographs. To make a tracing the cursor was positioned at the top of a fringe pattern or diffraction envelope with the single-slit, and then drawn through the center of the pattern and terminated at the opposing side.

D. Assay Chemistry

Figure 4A:
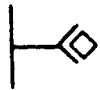
FIGS. 4a-4b is a flow chart of the important steps in forming a colloidal gold-labeled antibody (Au-antibody) sandwich assay for use in the apparatus of the invention.
Figure 4B:
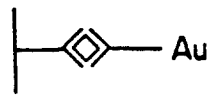
Figure 4C:
Figure 4F:
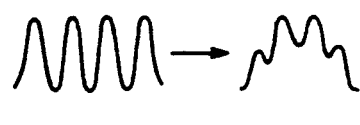

A flow chart of a first embodiment of the assay chemistry of the invention followed by the optical test is summarized in FIGS. 4a–g. In this assay the ligand is rabbit IgG which is incubated with a coverslip 14 (FIG. 4a) coated with anti-rabbit IgG, followed by incubation with a colloidal gold-labeled anti-ligand, such as, goat anti-rabbit IgG 40 (FIG. 4b). After a silver enhancement step, wherein the gold colloid nucleates precipitation of silver from a solution 42 as it comes into contact with the labeled antibody in the assay (FIG. 4c), the coverslip exhibits a deposition of darkly stained antibody-antigen complex. Insertion of this treated assay coverslip over one slit $S_2$ of a double-slit configuration produces loss of transparency through slit $S_2$ (FIG. 4d) resulting in loss of intensity $I_2$ of light from $S_2$ (FIG. 4e) and an observable, measurable loss of interference fringes (FIG. 4f). This loss in amplitude of fringes is then related to analyte concentration (FIG. 4g) in the quantification procedure described later in Section E.

The above general description of the methodology of the assay preparation is followed by the specific experimental example below:

The objective of the immobilization chemistry is covalent attachment of the anti-ligand, in this case a protein, which will selectively bind the target ligand or analyte. To prepare the glass for the immobilization chemistry the coverslip is acid treated to produce reactive silanol groups:

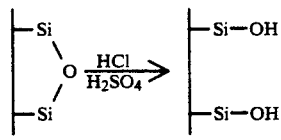

In a first example, this was accomplished as follows: Glass coverslips (81 mmz) were soaked in a 1:1 mixture of concentrated HCl and methanol, followed by several rinses with distilled $H_2O$. Coverslips were then soaked in hydrosulfuric acid for 30 min., followed by several rinses with distilled $H_2O$. Coverslips were boiled in distilled $H_2O$ for 30 minutes and then air-dried on low lint paper. (see Bhaia, S. K., Shriver-Lake, L. C., Prior, K. J., Georger, J. H., Calvert, J. M., Bredeborst, R., Ligler, F. S., Analytical Biochemistry, 178, 408–413, 1989.)

Next the glass is reacted with aminoethylpropyltriethoxysilane (APTES), to produce a reactive, amine-derivatized surface:

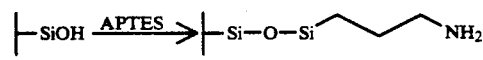

Specifically, a 2% solution (v/v) of APTES was prepared by mixing 200 ul of APTES in 9.8 ml toluene (dried over molecular sieves). The coverslips were soaked for 2 h, and rinsed in dry toluene. (see Weetal, H. H., "Methods of Enzymology", Mosach, K., Ed., Academic press: New York, 1976, Vol. XLIV, pp 139). The next step is the reaction of the amine derivatized glass with succinic anhydride to produce a carboxylic acid group on the surface:

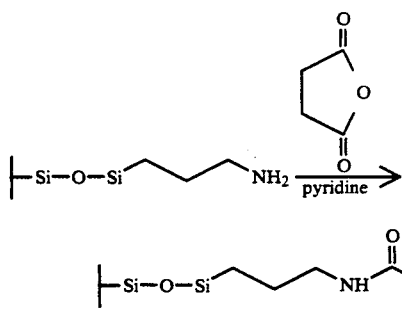

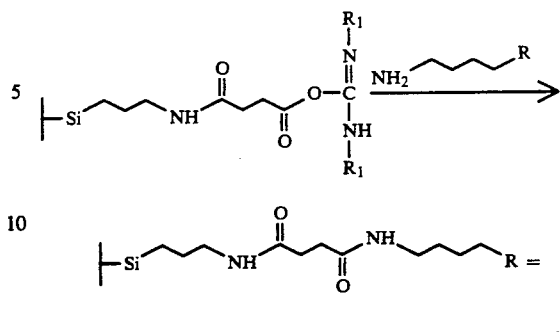

A solution of 0.20 g (2 mmol) succinic anhydride was combined with 40 mg (0.33 mmol) 4-dimethylaminopyridine in 6 ml anhydrous pyridine and divided into test tubes. The amine-derivatized glass coverslips were placed into the tubes, which were then sealed and shaken at room temperature for 16–20 hours. Coverslips were removed, rinsed with pyridine, methylene chloride and ether. If stored, they were placed in a desiccator over $P_2O_5$. (see Damha, M. J., P. A., Zabarylo, S. V., Nucleic Acid Research, 18 (13), 33813, 1990.) The glass is now ready for the carbodiimide chemistry which begins with activation of the succinylated surface with 1-ethyl-3-(3-dimethylaminopropyl) carbodiimide hydrochloride (EDC):

For the protein reaction a 0.05 mg/ml solution of anti-rabbit IgG was prepared by adding 73 ul of anti-rabbit IgG (4.1 mg/ml; commercially available from Sigma) to 6 ml borate buffer, which was then aliquotted into 6 test tubes. The coverslips were immersed, the test tubes were sealed and rocked gently overnight. The coverslips were removed and the supernatant was retained for absorbance measurements. For the blocking reaction the coverslips were then added to test tubes containing 1 ml 0.1 M ethanolamine (Bottle #5) and gently mixed for 30 min. The coverslips were then

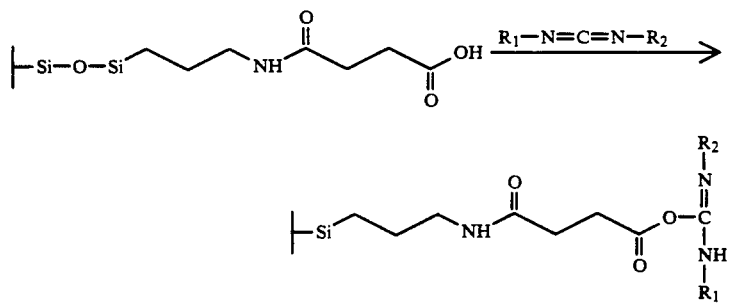

The procedure and reagents were those recommended with the Carbodiimide Kit for Carboxylated Microparticles (Polysciences, Inc., #19539). Carboxylated coverslips were soaked in carbonate buffer (Bottle #1) for 5 min, and then in phosphate buffer (Bottle #2) for 5 min. A 0.6 ml phosphate buffer was placed in test tubes with prepared coverslips. A 2% solution of carbodiimide solution was prepared by mixing 75.0 mg EDC with 3.75 ml phosphate buffer. 0.6 ml EDC solution was added, dropwise, to each of the test tubes containing the coverslips, and capped tightly. The solutions were shaken for 3.5–4 hours at room temperature. The coverslips were then removed and shaken in borate buffer (Bottle #4) for 5 min. followed by two more rinsings with borate buffer. The activated surface is then reacted with the alkylamine functional groups of the protein (anti-rabbit IgG) to be immobilized, forming an amide linkage:

transferred to 1 ml of BSA solution (Bottle #6) and gently mixed for 30 min. The coverslips were then rinsed in PBS and stored in storage buffer (Bottle #7) or PBS, 4–6 degrees.

The protein used as the anti-ligand can also be immobilized to a transparent plastic substrate that has been coated with a polymer containing residual carboxylate groups (Sera-Coat, Seradyn) for carbodiimide coupling.

For the assay, rabbit IgG was incubated with the anti-rabbit IgG coverslips, rinsed with PBS, and then treated with gold-labeled anti-rabbit IgG, and the silver enhancement step.

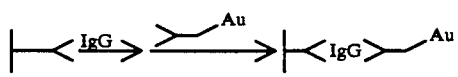

Specifically, the coverslips were rinsed with PBS two times. For ease of handling, a coverslip was positioned in the outer groove of a disposable cuvette and 20–40 ul of colloidal gold(30 nm)-labeled Goat anti-rabbit IgG (AuroProbe EM GAR G30, Amersham) was pipetted onto the surface and left for 60 min. The coverslip was then placed inside the same cuvette and rinsed thoroughly three times with PBS followed by three rinses with $H_2O$.

A silver enhancement step follows which produces a more dramatic decrease in the transparency of the reacted assay. In this step the gold nucleates precipitation of silver from a solution in the region of the labeled antibody:

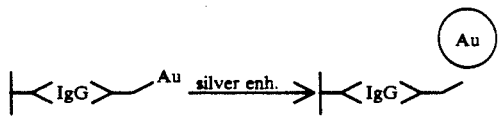

This was achieved using the IntenSE Silver Enhancement Kit (RPN.491, Amersham). A solution was prepared by combining equal number of drops from solutions A and B. The enhancement solution was pipetted into cuvettes containing individual gold-labeled antibody treated coverslips and reacted for 6-18 min. at room temperature. The coverslips were then rinsed with distilled H$_2$O. The reaction can be repeated to increase the effect.

E. Quantitation of the Assay

Equations have been derived for describing the dependency of the interference fringes on the luminescence intensities produced by the slits, and those equations can be employed in this detection method for quantifying the assay.

The equation for describing a quality termed the visibility ($V_1$) of the fringe pattern can be calculated by the relative intensities ($I_1$ and $I_2$) of the source light transmitted through the two identical slits ($S_1$ and $S_2$), as shown in FIG. 1 and can be calculated thusly:

$$V_1 = \frac{2\sqrt{I_1}\sqrt{I_2}}{I_1 + I_2} |\gamma_{12}| \qquad \text{Eq. (2)}$$

where $I_1$ and $I_2$ are the intensities at point P from the radiation passing through the slits 1 and 2 when viewed independent of each other, and $|\gamma_{12}|=1$ is a coherency limit for a laser source.

The visibility ($V_2$) can also be calculated by the intensity of the fringes:

$$V_2 = \frac{I_{max} - I_{min}}{I_{max} + I_{min}} \qquad \text{Eq. (3)}$$

where $I_{max}$ and $I_{min}$ are the intensities corresponding to a maximum and an adjacent minimum in the fringe system. $I_{max}$ and $I_{min}$ are functions of the light intensities transmitted through the slits $S_1$ and $S_2$:

$$I_{max} = I_1 + I_2 + 2\sqrt{I_1 I_2} |\gamma_{12}| \qquad \text{Eq. (4)}$$

$$I_{min} = I_1 + I_2 - 2\sqrt{I_1 I_2} |\gamma_{12}| \qquad \text{Eq. (5)}$$

Since $I_{max}$ and $I_{min}$ are determined by $I_1$ and $I_2$ then it follows that the two visibility equations should produce identical values ($V_1 = V_2$).

If the intensity for $I_1$ is held constant while the intensity of $I_2$ is reduced one can calculate the change in the fringe pattern. Table 4 contains values for a model system where the intensity ($I_1$ and $I_2$) through each slit are assigned a value of 10. When the intensity is identical through each slit the upper value of 1.0 exists for $v_2$; as the intensity, $I_2$, is decreased the $V_2$ decreases towards 0.0. When $V_2=1.0$, the fringe pattern has the maximum amplitude of $I_{max}$ and a complete loss of amplitude at $I_{min}$. As $V_2$ moves towards 0.0 the fringe pattern collapses to the diffraction envelope.

TABLE 4

THE CHANGES IN $I_{MAX}$ AND $I_{MIN}$ WITH LOSS OF TRANSMISSION THROUGH ONE SLIT

| $I_1$ | $I_2$ | $I_{max}$ | $I_{min}$ | $V_2 = \frac{I_{max} - I_{min}}{I_{max} + I_{min}}$ | Group |
|---|---|---|---|---|---|
| 10 | 10 | 40.0 | 0 | 1.0 | A |
| 10 | 9.5 | 38.99 | 0.006 | 0.999 | |
| 10 | 9.0 | 37.97 | 0.026 | 0.998 | |
| 10 | 8.0 | 35.88 | 0.111 | 0.993 | |
| 10 | 7.0 | 33.73 | 0.266 | 0.984 | |
| 10 | 6.0 | 31.49 | 0.508 | 0.968 | |
| 10 | 5.0 | 29.14 | 0.86 | 0.94 | B |
| 10 | 2.0 | 20.94 | 3.05 | 0.74 | C |
| 10 | 1.0 | 17.32 | 4.68 | 0.57 | D |
| 10 | 0.1 | 12.10 | 8.10 | 0.19 | E |
| 10 | 0.001 | 1.69.38 | 0.063 | | F |

Figure 5:
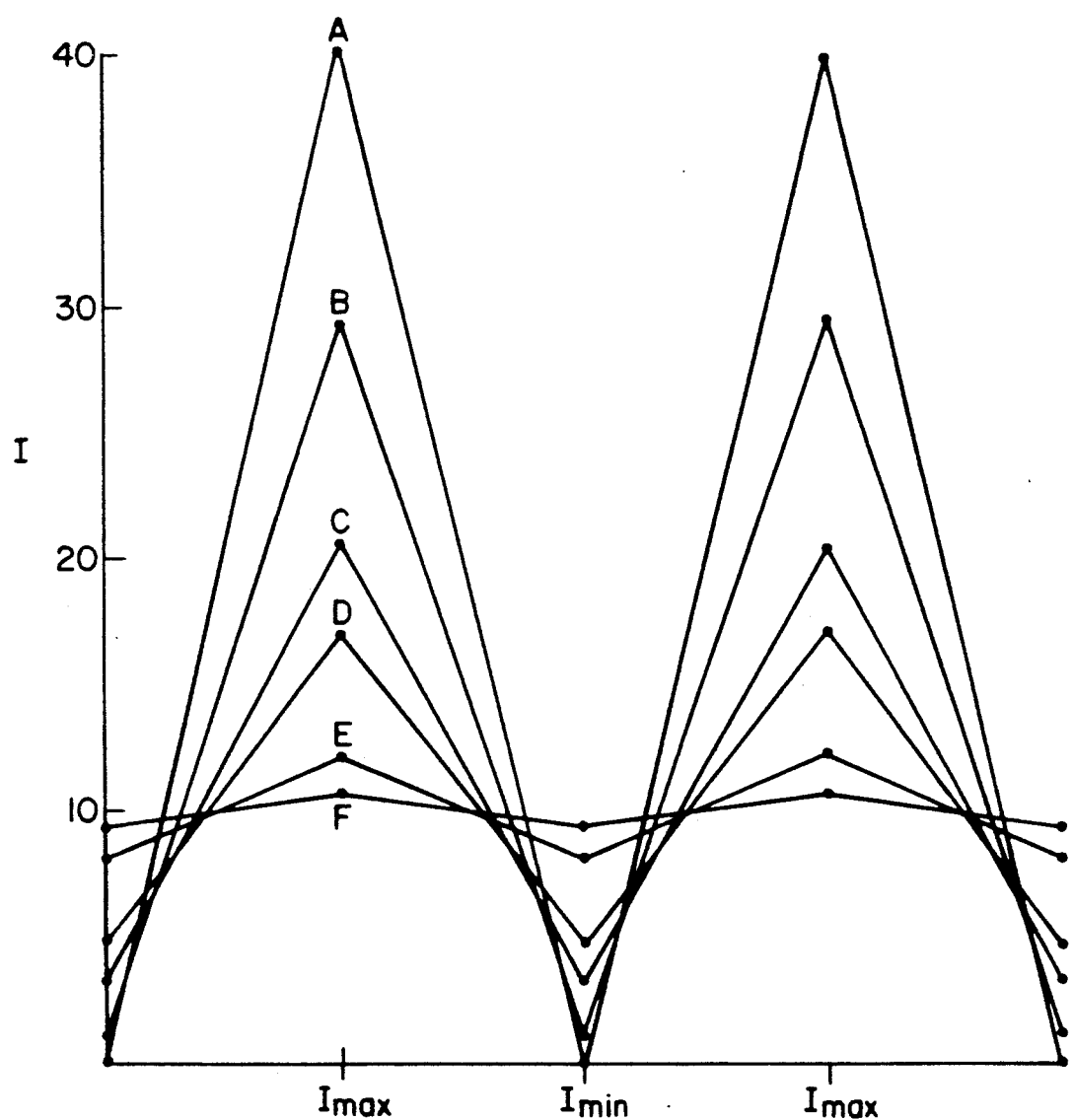
FIG. 5 is a plot of the intensity of two adjacent maxima of double-slit interference pattern showing the change caused by varying the transmission through one slit.

A graph of two adjacent fringes is shown in FIG. 5. The line labeled A describes the intensities of $I_{max}$ and $I_{min}$ formed by two equal, unobstructed slits. The lines B through F show the change in amplitudes as the intensity through one slit is decreased. At the $I_{max}$ for line F the intensity amplitude is almost 10, which is the intensity of light passing through the unobstructed slit, or $I_1$.

It is important to appreciate that the summation of the two slit intensities ($I_1+I_2$) without the phenomenon of constructive interference, would be, in FIG. 5, a value of 20. Thus, the intensity of $I_{max}$ observed in lines A through C, where the amplitude is greater than 20, is due to constructive interference. Thus, the amplitude values between 20 and 40 represent an increased signal content for the correlation of assay information.

The intensity of $I_{max}$ at point P can also be quantified from the attenuation of $I_2$ due to a change in absorbance ($\Delta A = \Delta \epsilon bc$) of the sample. The existing formulas which govern absorbance spectroscopy can be linked with the formulas used for evaluating interference phenomena since both methodologies are based on transmission intensity of a source and the resultant intensity due to passing the radiation through a sample.

Transmission, T, is defined as the ratio of the intensity of unabsorbed radiation, I, to the intensity of the incident radiation, $I/I_0$. From Beer's Law, exists the relationship between $\epsilon bc$ and T, where $\epsilon =$ the extinction coefficient of the absorbing species, b= path length of cell, and c=concentration of species:

$$\frac{I}{I_0} = 1^{-\epsilon bc} = 10^{-A} \qquad \text{Eq. (6)}$$

In the proposed configuration for measuring interference phenomena the $I_2$ transmission intensity can be viewed as a ratio of the intensity of unabsorbed radiation to the intensity of incident radiation, $I_X/I_O$:

$$I_1 = \text{unmodulated beam} = I_0 \qquad \text{Eq. (7)}$$

$$I_2 = \text{assay beam} = \frac{I_x}{I_0} \qquad \text{Eq. (8)}$$

From Eq. 6:

$$\frac{I_x}{I_0} = 10^{-\epsilon bc}$$

$$I_x = I_0 \, 10^{-\epsilon bc} \qquad \text{Eq. (9)}$$

Substitution of the preceding identities into the $I_{max}$ equation results in an $I_{max}$ expression as a function of absorbance defined by $\epsilon bc$ for a particular species:

$$I_{max} = I_1 + I_2 + 2\sqrt{I_1 I_2} \qquad \text{Eq. (10)}$$

$$I_{max} = I_0 + \frac{I_x}{I_0} + 2\sqrt{I_0 \frac{I_x}{I_0}} \qquad \text{Eq. (11)}$$

$$I_{max} = I_0 + \frac{I_x}{I_0} + 2\sqrt{I_x} \qquad \text{Eq. (12)}$$

$$I_{max} = I_0 + 10^{-\epsilon bc} + 2\sqrt{I_0 \cdot 10^{-\epsilon bc}} \qquad \text{Eq. (13)}$$

Figure 6:
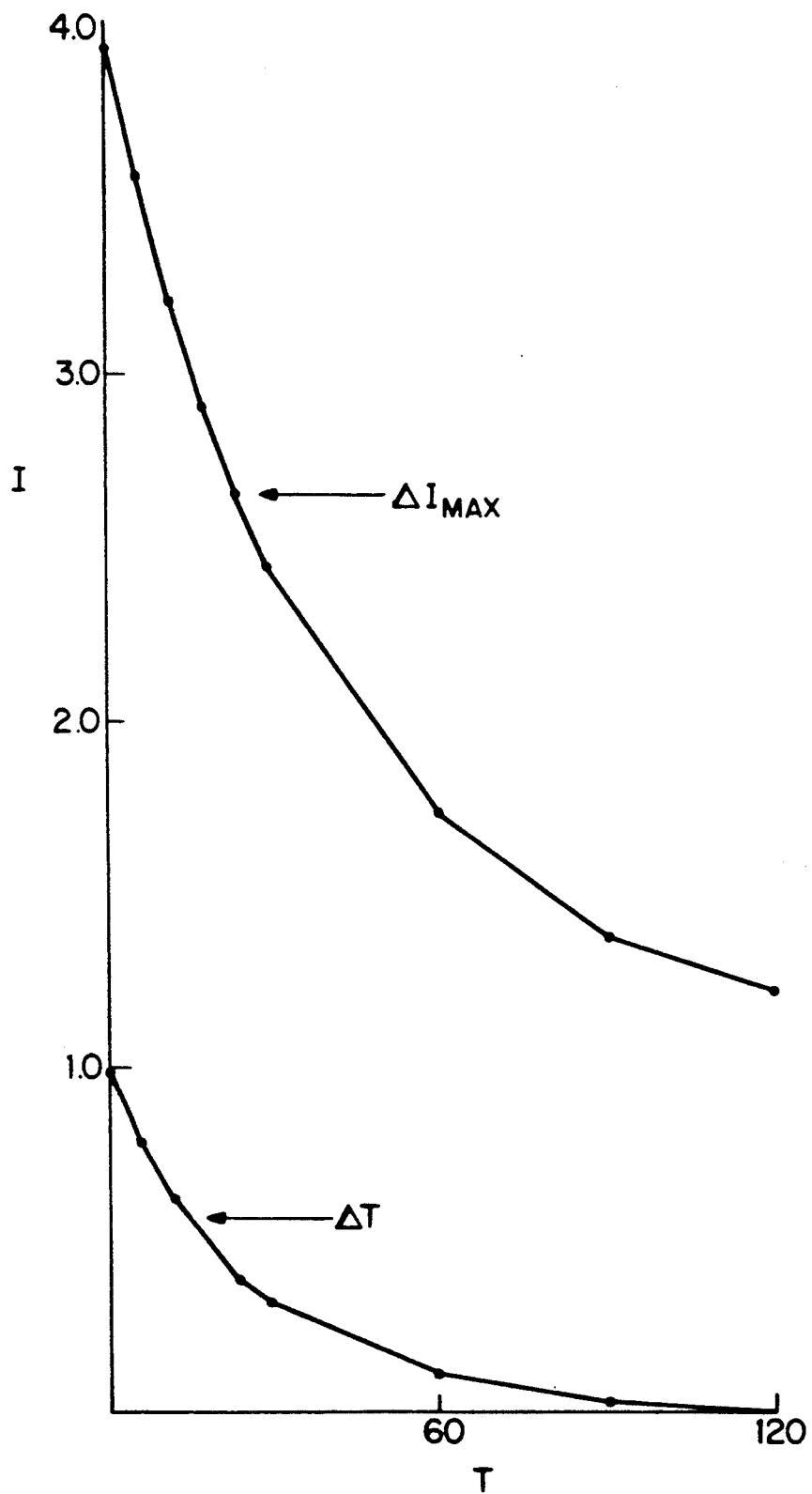
FIG. 6 are plots of intensity I versus transmission T for changes in $I_{max}$ (curve $\Delta I_{max}$) and changes in transmission (curve $\Delta T$).

Of interest is a comparison of the relative signal change of both $\Delta T$ and $\Delta I_{max}$ for identical sample concentration and volume. The transmission values for an absorbance series ($\Delta \epsilon bc$) as measured in a standard spectrophotometer are shown in Table 5, along with the $I_{max}$ values calculated from Eq. 13 for the same series. Both functions, $\Delta T$ and $\Delta I_{max}$, are plotted in FIG. 6. For any given concentration change the $\Delta I_{max}$ function has a greater dynamic range than the $\Delta T$ function for the same variation in $\epsilon bc$. For example, the change in concentration between 0.25 and 0.50 absorbance units will produce a $\Delta I_{max}$ of 0.55 units of intensity change and a $\Delta T$ of 0.23 units of intensity change. Therefore, the $\Delta I_{max}$ function would be more than 2 times as sensitive as the $\Delta T$ function. The increased dynamic range results form the fact that Eq. 13 contains two terms which change as a function of absorbance modulation. Since sensitivity of spectroscopic analysis is defined by the magnitude of absorptivity as well as the minimum absorbance which can be measured with the required degree of certainty, the $\Delta I_{max}$ function would provide greater spectrophotometric sensitivity.

TABLE 5

$I_{MAX}$ VALUES CALCULATED FROM AN ABSORBANCE SERIES

| $\epsilon bc$ | $T = 10^{-\epsilon bc}$ | $2\sqrt{I_0 \cdot 10^{-\epsilon bc}}$ | $I_0$ | $I_{max}$ |
|---|---|---|---|---|
| 0.1 | 0.977 | 1.976 | 1.0 | 3.95 |
| .1 | 0.794 | 1.782 | 1.0 | 3.57 |
| .2 | 0.630 | 1.587 | 1.0 | 3.21 |
| .3 | 0.501 | 1.415 | 1.0 | 2.91 |
| .4 | 0.398 | 1.261 | 1.0 | 2.66 |
| .5 | 0.316 | 1.124 | 1.0 | 2.44 |
| 1.0 | 0.100 | 0.632 | 1.0 | 1.73 |
| 1.5 | 0.031 | 0.352 | 1.0 | 1.38 |
| 2.0 | 0.010 | 0.200 | 1.0 | 1.21 |

F. Dynamic Range of the Optical Detection System

The dynamic range of a signal transduction mechanism is understood to be the degree of change of signal per unit of change in concentration of the analyte:

$$\text{Dynamic range} = \frac{\Delta \text{ signal}}{\Delta \text{ concentration}}$$

As the degree of signal change per concentration change increase so does the detectability of the signal as well as the accuracy or resolution of the concentration measurements.

Figure 7B:
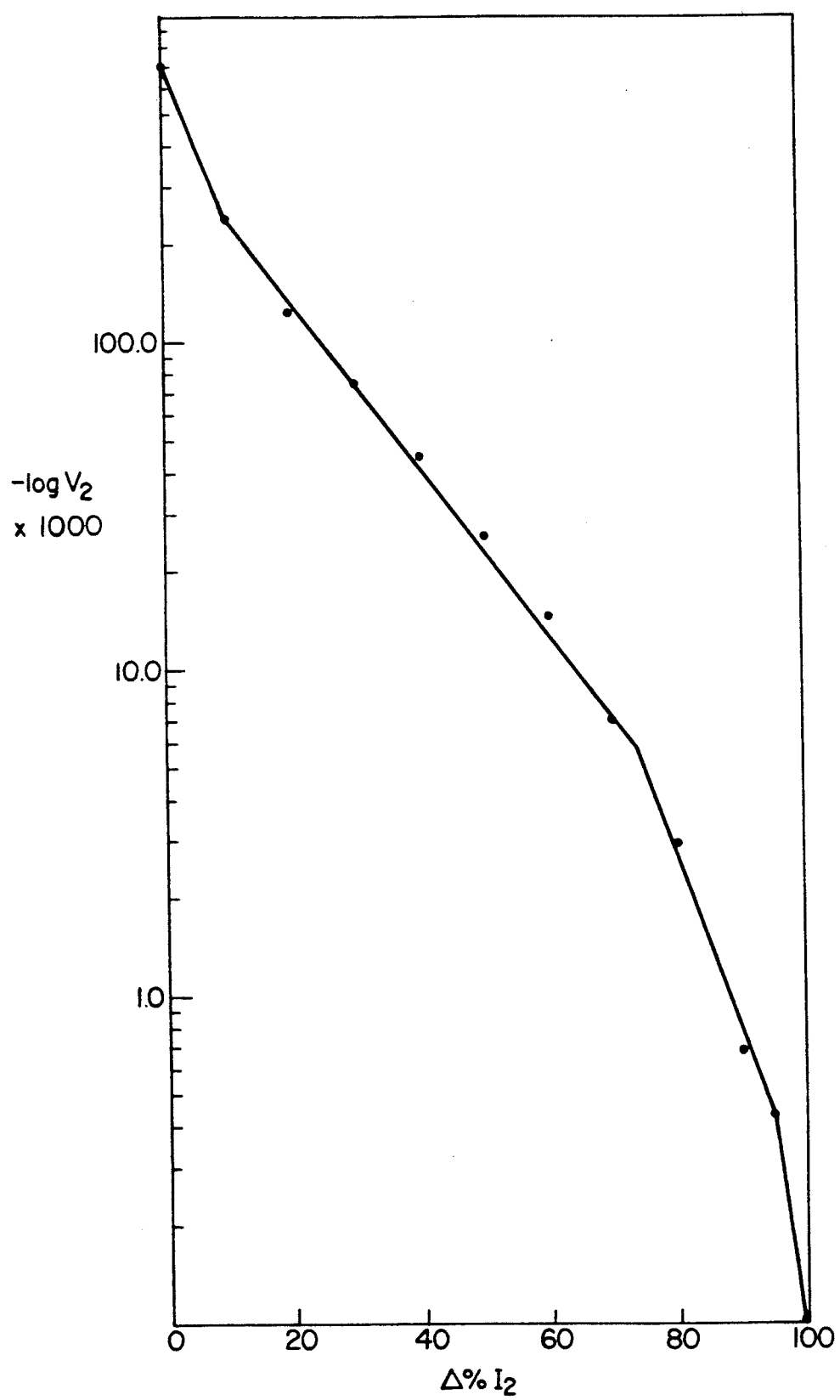
FIG. 7(b) is a plot of the $-\log V_2 \times 1{,}000$ versus $\Delta\%$ $I_2$.

The $V_2$ (Eq. 3) is plotted in FIG. 7($a$) as a function of the percent of transmission $I_2\%$) through the second slit ($S_2$) (Table 4). At 100% transmission, equal intensities pass through two identical slits and the fringe pattern has the most defined fringes, where $I_{max}$ is at its highest value and $I_{min}$ is zero. At 0% complete loss of the fringe pattern occurs and only the diffraction envelope remains. On the graph shown in FIG. 7($a$) one can arbitrarily assign 40 units on the visibility scale. In the assay, the change in transmission through $S_2$ is a function of the concentration of analyte bound to the coverslip, and therefore the $I_2\%$ is the concentration component. The dynamic range is therefore:

$$\text{Dynamic range} = \frac{\Delta V_2}{\Delta I_2\%} \qquad \text{Eq. (14)}$$

One can see by the graph of FIG. 7($a$) that this relationship is not fixed but changes rather drastically as the $\Delta I_2\%$ approaches zero. Of the 40 units of signal division a loss of 50% transmission in $I_2$ produces a visibility change from 1.0 to 0.94, or 2.5 units of signal. The dynamic range would be 0.05, calculated thusly:

$$\frac{\Delta V_1}{\Delta I_2\%} = \frac{2.5}{50} = 0.05$$

A loss of transmission in $I_2$ from 50% to 0% produces a visibility change from 0.94 to 0.0, or 37.5 units of signal, and an increase of dynamic range to 0.75. Thus, one can see that the dynamic range is clearly a function of the degree of transmission loss and it increase significantly as the transmission approaches zero. A more linear plot of the Visibility ($V_2$) data can be generated by plotting $-\log V_2 \times 1000$ against $\Delta\% I_2$, which is shown in FIG. 7($b$).

Figure 8:
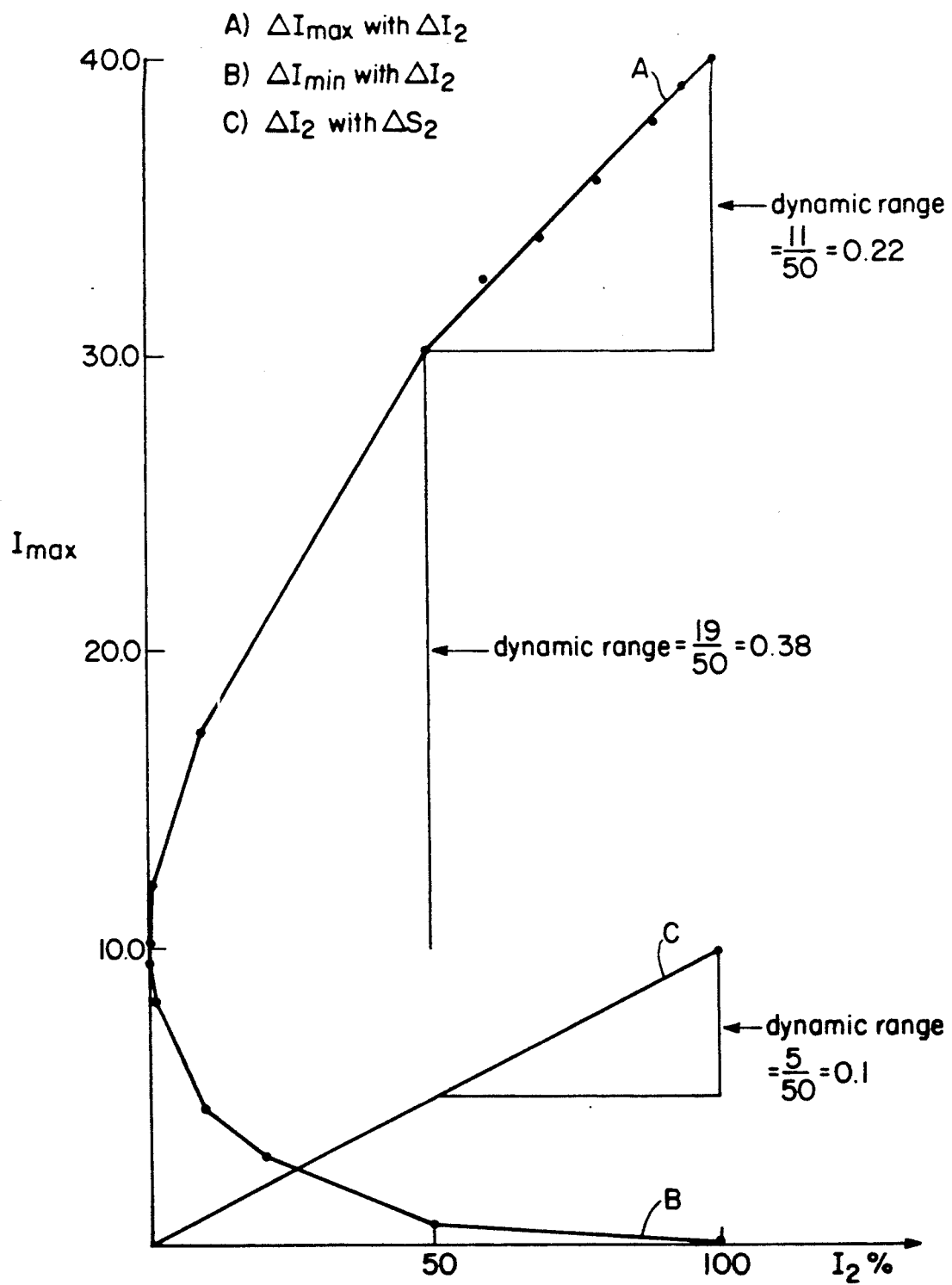
FIG. 8 is a plot of the change in $I_{max}$ and $I_{min}$ as a function of change in transmission $I_2$ through slit $S_2$.

However, the change in fringe visibility is not the only useful function for calculating a dynamic response. Using the model and values from Table 4, the change in $I_{max}$ and $I_{min}$ as a function of $\Delta I_2\%$ is shown in FIG. 8. Where there is no loss of transmission the $I_{max}$ is at its highest amplitude, 40.0, and the $I_{min}$ is at its lowest amplitude, 0.0. With complete loss of transmission both values approach identical values of 10.0, which is the intensity through one open slit. If the $I_2\%$ changes form 100 to 50% the dynamic range in terms of $I_{max}$ is 0.22;

$$\text{Dynamic Range} = \frac{\Delta I_{max}}{\Delta I_2\%} = \frac{11}{50} = 0.22 \qquad \text{Eq. (15)}$$

which is significantly greater than the dynamic range calculated in terms of $\Delta V_2$, as plotted in FIG. 7($a$). The dynamic response of the $I_{min}$ over the same range is 0.012. Now, if the transmission loss creates a $\Delta I_2\%$ of 50% to 0% the dynamic range in terms of $I_{max}$ becomes 0.38.

Again, these calculations are made over large, arbitrary segments of the graph and are gross averages. But they do indicate that an appreciation of the dynamic range must be associated with a specified form of the signal measurement (V or $I_{max}$) and must be carefully calibrated over the full percentage of transmission loss.

Nevertheless, both of these graphs indicate that a significantly changing function can be correlated with a change in percent of $I_2$ transmission and its contribution to fringe pattern values can be subsequently correlated with analyte concentration.

A very interesting aspect of this detection method should be considered at this point. Also plotted in FIG. 8 is the function C which represents the loss of intensity of $I_2$ if monitored independently. A decrease from 100 to 50% transmission produces only 5 units of signal change and has a dynamic range of 0.10. The change from 50 to 0% transmission has the same number of signal units and thus the same dynamic range. Therefore 0.1 is the limiting dynamic range for a linear loss of transmission measurement and this is considerably less than the dynamic range produced by a transduction mechanism based on a changing amplitude of an interference fringe, as described in the preceding analyses of the graphs in FIGS. 7 and 8.

Therefore, the slit format, in principle, is more sensitive than straight optical density. This enhanced sensitivity can be appreciated by comparing the relative resolutions of the measurements. Resolution is conventionally taken as the inverse of the dynamic range. For a dynamic range of 0.10, as calculated for the linear loss of transmission, the resolution, or number that can be measured with certainty, would be 10.00. For a dynamic range of 0.22, as calculated for the change in $I_{max}$ from 100 to 50% loss of transmission, the resolution would be 4.54, meaning that the certainty of the measured value would be to a smaller number than the preceding case, and thus more accurate. A dynamic range of 0.75 has a resolution of 1.33, providing even more accuracy.

The sensitivity of this assay is defined by the number of target molecules required to obstruct the transmission through $S_2$ to produce a measurable change in the fringe pattern. Several factors will contribute to the ultimate sensitivity:

1. The size of the slit.
2. The limiting concentration of immobilized antiligand on the coverslip.
3. The limiting concentration of analyte and gold labeled-antibody coupled to the assay surface from the solution.
4. The contribution of the silver precipitation step to the transmission loss.
5. The ability to make a kinetic measurement with the silver precipitation reaction.

An analysis of potential sensitivity was based on a paper (Bhatia et al. Anal. Biochem. 178. 408, 1989) that optimized covalent immobilization of antibody to a glass surface. The concentrations of bound antibody to both coverslip and optical fiber substrates are shown below.

| COMPARISON OF ANTIBODY BINDING TO COVERSLIP AND FIBER | | |
|---|---|---|
| Area | Coverslip 968 mm² | Optical Fiber 74 mm² |
| Antibody immobilized | 638 ± 134 ng (0.66 ng/mm², 4 fmol/mm²) | 71 ± 3 ng (0.96 ng/mm², 6 fmol/mm²) |
| Specific antigen binding | 350 ± 50 ng (0.36 ng/mm²) | 27 ± 4 ng (0.36 ng/mm²) |

For a slit of size 5 $\mu m \times 100$ $\mu m$, a sensitivity of 6'10⁵ molecules may be calculated as follows:

Split size: 5 $\mu m \times 100$ $\mu m = 500$ $\mu m^2 = 500 \times 10^6$ $nm^2$
Maximum antibody immobilized on slit area:

$$\frac{4 \text{ fmol}}{10^6 \mu m^2} = \frac{x}{500 \mu m^2}$$

$x$ = 0.002 fmol
Antigen capture (50%) = 0.001 fmol
= 6 × 10⁵ molecules
Labeled antibody capture (50%) = 0.0005 fmol
= 3 × 10⁵ molecules The area of the colloid gold label of 30 nm:

Area = $\pi r^2$
= 706.5 $nm^2$

The theoretical number of molecules required to cover the entire slit can be estimated by:

$$\frac{\text{Area of slit}}{\text{Area of gold colloid}} = \frac{500 \times 10^6 \text{ nm}^2}{706.5 \text{ nm}^2/\text{molecule}} = 7 \times 10^5 \text{ molecules}$$

$$\frac{\text{Ratio of experimentally captured antibody}}{\text{Theoretical requirement for slit coverage}} = \frac{3 \times 10^5 \text{ molecules}}{7 \times 10^5 \text{ molecules}} = 0.43$$

However, this theoretical treatment does not include the effect of the silver precipitation step, which appears to make the most significant contribution in the change of intensity of the coverslip. If $3 \times 10^5$ molecules of gold-labeled antibody covers 43% of the slit, a reduction of the transmission to 57% should reduce the intensity of $I_{max}$ by ca.25% (FIG. 8). The silver precipitation may extend the sensitivity well below this estimation of $3 \times 10^5$ molecules. In some of the experiments no gold-labeled antibody was observable by the naked eye on the coverslip until after the precipitation step, at which point the coverslip became significantly opaque.

The detection method of the invention possesses a number of substantial advantages. The signal output is in the form of both an amplitude parameter and a pattern formation which offers greater information content for data analysis over a system based only on intensity measurement. For an interference assay, the signal, in the form of the entire interference pattern, may be stored in computer memory and compared with a computer standard so that a microscopic alteration to the assay standard pattern, detectable only through computerized treatment, could deliver an exquisitely sensitive diagnostic.

Another advantage of the transduction method of the invention is that the amplitude component in the form of $I_{max}$ has been increased fourfold over a direct measurement of intensity, due to the contribution of the two individual wavefronts as well as the constructively interfering electromagnetic waves. Again, this increases the information content of the potential signal which should increase the dynamic range and thus the sensitivity of the assay. A sensitivity of less than 10⁵ molecules is possible which would equal or exceed the sensitivity of isotopic methods.

Another underlying quality which should make this methodology very competitive with other detection techniques is the simplicity of its optical design and principles as well as ease of assay procedure. Such simplicity can lead to ruggedness as well as economy. A compact bench top instrument should be easily manufacturable, with the assay chemistry incorporated into a disposable dipstick. For use with gold-labeled antibody reagents, the dipstick would require incubations with sample, gold-labeled antibody, and silver enhancement solutions, which could be accomplished in 1-2 hours. For use with a bacterial cell, simple incubation with the sample, followed by rinsing would complete the procedure. (It may be possible that as few as 2-3 bound cells would suffice to alter the fringe pattern).

And finally, this is a generic system which could be used for any clinical or environmental samples participating in specific, recognition events. Assays based on immunochemistry and DNA would be the initial areas of development. Eventually other molecular recognition systems, such as chemical receptors, cyclodextrins, or ion-selective membranes, may be incorporated into analytical applications. This system could also be used in the study of material science processes, such as monitoring crystal growth, photo-induced polymerizations, and surface film depositions.

G. Alternate Embodiments

Numerous variations of the basic embodiment previously described are contemplated. For example, the slit number and shape may be varied. The present preferred embodiment is a double-slit formed of two identical, parallel slits, but predictable interference phenomena can be produced by other numbers of identical slits. With more than two slits it would be possible to assign individual assays to a different slit or test assays in each slit would be for multiple analytes with a single procedure.

Although the visibility equations previously described are not derived for non-identical parallel slits, it may be possible that this assay would be enhanced with non-identical slits.

Also, holes may be used in place of slits to form a circular interference pattern. For example, two pinholes will also produce interference fringes and can be precision made to about 2 $\mu$m in diameter, which would give a smaller total surface area than the proposed slits (and thus enhance sensitivity). The assay chemistry could be performed as drops on the pinhole, therefore using very minute sample volumes.

The assay occurring on the glass coverslip 50 could also serve to produce two slits $S_1$ and $S_2$ from a single slit $S_0$ as shown in FIG. 9a-9d. In this case the antiligand $S_2$ is immobilized on an edge of the coverslip (FIG. 9(b)). The assay would darken the edge of the coverslip, FIG. 9(c), which would then be positioned over the single slit $S_0$ FIG. 9(a) as shown in FIG. 9(d) forming two slits $S_1$ and $S_2$.

The assay chemistry could be centralized on a glass slit 90 so that gold-labeled antibody assay forms a double slit 92 as shown in FIG. 10.

It is also possible, as shown in FIG. 11, to produce double-slit interference fringes by optical configurations that create virtual slits. Although the principle of the assay would be the same as heretofore described, the alteration of transmission would require interference with the geometry producing the virtual slit.

In this arrangement light rays from a single slit $S_1$ pass to the screen 80 via two paths, one of which is direct, A—A, and the other of which is an indirect path, B—B, created by reflection from a mirror M placed in the center line C/L so as to produce a reflection which would appear to emanate from a slit $S_2$ located equidistant from center line C/L. The source is therefore viewed by two paths, one direct and one reflected at a glancing angle in a mirror. The reflection reverses the phase 180°, but otherwise the analysis and the fringes are the same. The area of reflection on the mirror would be the location of the assay chemistry, which would cause appearance or loss of reflection.

The previous configuration involves use of a Lloyd's mirror. A Fresnel's mirror can be used as in FIG. 12 to produce two virtual slits which are formed with a point source S projected on two plane mirrors, $M_1$ and $M_2$, mutually inclined at a small angle.

The two resulting virtual images, $S_1$ and $S_2$, act as coherent sources. The separation of $S_1$ and $S_2$ is defined:

$$d = 2b \sin \alpha$$

where $\alpha$ is the angle between the mirrors. Again the assay would be placed on one of the mirrors and the resultant change in reflectivity used to correlate the analyte concentration.

Two equal prisms when placed together, base to base as in FIG. 13, with their refracting edges parallel, form a Fresnel bi-prism and will divide a cone of light from source S into two overlapping cones. The prisms thus form two virtual slit images, $S_1$ and $S_2$. A so-called Billet's split lens arrangement formed by two convex lens can form two images, both of which are real as shown in FIG. 14.

With all of these optical arrangements, interference fringes are formed in the region defined by the diverging cones from the sources $S_1$ and $S_2$. Assays could be developed which altered the optical arrangement, thus altering fringe patterns. For example, application to the Lloyd's mirror (FIG. 11) or Fresnel's mirror (FIG. 12) configurations would require location of the assay chemistry in the region of reflection on the mirror, which produces the virtual slit. If the assay chemistry resulted in a loss of reflectivity of the mirror's surface the intensity of reflected light would decrease and the interference pattern would be modulated. Application to the Fresnel bi-prism (FIG. 13) or Billet's split lens (FIG. 14) would require location of the assay chemistry on one of the prisms or lenses so that the post-assay intensity of diffracted radiation would no longer equal the intensity diffracted by the other optical unit in the pair.

As shown in FIG. 15, reactions could be monitored by use of a transport flow-cell microcell 94 which would build up an interfering absorbance on screen 96. In FIG. 15, B is a reference cuvette, A is an assay cuvette, and they are divided by the cuvette separation, C. The progress of the reaction produces a molecular population that would either remain in the flow cell A or become entrapped on its surface, and thus make the transmitted light non-identical to that passing through cell B.

Another configuration would have slits $S_1$ and $S_2$ incorporated into a transport flow cell 86 as in FIG. 16. The cell 86 is disposed opposite a source 85. Antiligand would be immobilized on $S_1$ and buildup of ligand on its surface would alter the fringe pattern as seen by the detector 87.

The dynamic range of the detection system may be enhanced not only by increasing the number of slits, but by increasing the number of slits covered by the assay.

Table 6 below shows how the intensity of the principle maxima increases as a function of $N^2$ times the intensity $I_o$ of one slit.

TABLE 6

INTENSITY OF PRINCIPAL MAXIMA FROM N SLITS IS $N^2 \times I_o$

| # Slits | I | $I_o = 10$ |
|---|---|---|
| 1 | $I_o$ | 10 |
| 2 | $4I_o$ | 40 |
| 3 | $9I_o$ | 90 |
| 4 | $16I_o$ | 160 |
| 5 | $25I_o$ | 250 |
| 6 | $36I_o$ | 360 |
| 7 | $49I_o$ | 490 |

Figure 19:
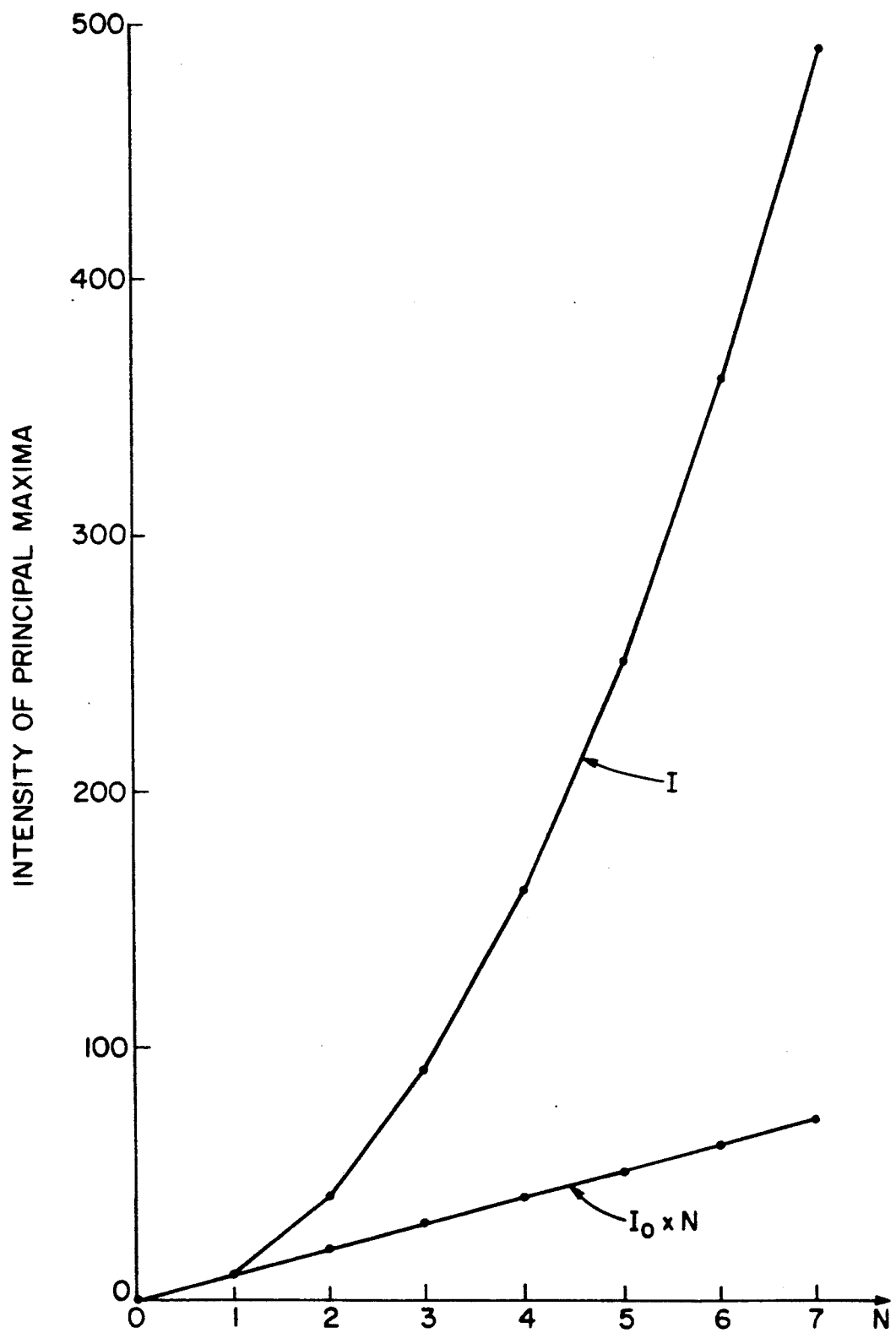
FIG. 19 is a plot of the intensity of the principle maxima $I_o$ versus the number of slits.

FIG. 19 is a plot of the data from Table 6. As shown in FIG. 17, if the assay slide 100 covers 5 out of 6 slits 104 of the mask 102 the intensity range increases by 350 units; instead of 1 of 2 in which case as follows: 6 slits, I=360, 1 slit I=10, the change $\Delta=350$ whereas in the two slit system $\Delta=30$ as follows 2 slits I=40, 1 slit I=10, and $\Delta=40-10$ or 30.

If only 3 slits are covered on a 6 slit mask as in FIG. 18 the resultant $\Delta=270$ computed as follows:

```
6 slits, I = 360
3 slits, I =  90
    Δ    = 270
```

Note: The slits dedicated to the assay need not be adjacent.

The assay substrate 60 could also contain the slits $S_1$ and $S_n$ (FIG. 20(a)) with the anti-ligand 62 immobilized to one of the slits (i.e. $S_1$). The as reaction causes slit $S_1$ to become less transparent (FIG. 20b). In this embodiment the optical radiation is passed through identical slit material, preserving the symmetrical phases of the two wavefronts. Also, any nonspecific binding of protein from the sample would occur equally in the regions of $S_1$ and $S_2$, again preserving the symmetry of $I_1$ and $I_2$ since both intensities would be identically altered by the contaminating material.

FIG. 21(a) and 21(b) illustrates alternate embodiments in which the mask or assay slit 70/70' is square shaped (FIG. 21a) or triangular (FIG. 21(b)) in shape. A single square slit will produce an interference pattern 72 as shown in FIG. 21(a) Likewise, a single triangular shaped slit 70' produces the pattern 72' of FIG. 21(b).

By immobilizing anti-ligand 74 on a diagonal half of square slit 70 as in FIG. 21(c) and reacting the anti-ligand with an appropriate ligand in an assay, the square slit 70 becomes a triangular slit FIG. 21(d), and a triangular based diffraction pattern 72' occurs FIG. 21(b). A detector (not shown) monitors the appearance of the new diffraction pattern 72' to determine the presence and concentration of the ligand.

Equivalents

Those skilled in the art will recognize, or be able to ascertain, using no more than routine experimentation, many equivalents to the specific embodiments of the invention described herein.

These and all other equivalents are intended to be encompassed by the following claims. For example, while the invention has been described in connection with light waves in the visible spectrum, the invention is applicable to any electromagnetic waves throughout the entire spectrum

We claim:

1. A method for determining the presence and/or concentration of one or more analytes in a sample, in which each analyte to be determined is capable of being recognized as a ligand by at least one antiligand, comprising the steps of:
    a) providing one or more assay substrate(s), each comprising a transparent surface which is coated with an antiligand capable of binding an analyte;
    b) reacting the sample with each provided assay substrate under conditions sufficient to cause each analyte whose presence or concentration is to be determined, if and when present in the sample, to bind to the surface coated with its corresponding antiligand;
    c) reacting each surface form step b) with an antiligand specific for the analyte immobilized thereon under conditions sufficient to cause the introduced antiligand to bind to the surface substantially only if and when analyte is bound to the surface;
    d) providing an opaque mask containing two or more transparent apertures through which light may be projected to form an interference pattern;
    e) determining the interference pattern formed when light is projected through apertures substantially identical to the apertures of the mask provided in step d);
    f) positioning each assay substrate so that the surface treated in steps b), and c) covers at least one of the apertures of the mask provided in step d), with the proviso that at least one of the apertures of the mask remains uncovered;
    g) determining the interference pattern formed when light is projected through the apertures after the positioning of the surface in step f) and
    h) correlating changes in one or more features of the interference patterns of step e) and g) with the presence and/or concentration of an analyte in the sample.

2. A method according to claim 1 wherein the apertures are slits.

3. A method according to claim 1 including further treating each surface form step c) so that at least one optical characteristic of each surface is altered substantially only if, when and where the antiligand introduced in step c) is bound to the surface and wherein said further treatment comprises a chemical reaction resulting in the deposition or localization of optically dense or opaque material on the initially transparent surface.

4. A method according to claim 3 wherein said optically dense or opaque material is formed by the deposition of silver grains at the loci or colloidal gold particles associated with an antiligand-analyte complex.

5. A method according to claim 3 wherein the reaction product formed pursuant to said further treatment is a chromophore or pigment, and the light is selected to be of a wavelength which interacts with that chromophore or pigment.

6. A method according to claim 5 wherein multiple analytes are determined using a single analytical assay surface coated with multiple antiligands corresponding to the multiple analytes by the employment of distinct chromophores, each with a substantially non-overlapping absorption spectrum with respect to other chromophores used, associated with the antiligands introduced in step c) for each analyte to be determined.

7. A method according to claim 3 wherein said optical characteristic is selected form the group comprising scattering, absorption, phase shift, refraction or polarization of the incident light.

8. A method according to claim 1 wherein the antiligand of step c) is conjugated with colloidal gold.

9. A method according to claim 1 wherein the optical characteristic of the surface is altered by the attachment of an item selected from the group comprising bacteria, polymeric particles, and cells.

10. A method according to claim 1 wherein the light is monochromatic.

11. A method according to claim 1 wherein the light is coherent.

12. A method according to claim 1 wherein the number of apertures is two.

13. A method according to claim 1 wherein multiple analytes are simultaneously determined by providing multiple analytical assay surfaces, each specific for a particular analyte, and in step f) positioning each analytical assay surface over one or more apertures.

14. A method according to claim 1 wherein any of the antiligands employed is selected from the group comprising antibodies, antigens, nucleic acids, chemical receptors, cyclodextrins, and ion selective membranes.

15. A method according to claim 1 wherein the correlation in step i) is made by comparison of the change in the assay to changes resulting form separately analyzed reference samples of known composition.

16. A method according to claim 1 wherein the feature(s) used for comparison of the interference patterns is selected form the group comprising visibility, $I_{max}$, $I_{min}$, and mathematical functions of one or more of visibility, $I_{max}$, and $I_{min}$.

17. A method according to claim 1 wherein one or more of the apertures is a virtual aperture.

18. A method according to claim 17 wherein the virtual aperture(s) are produced by a device selected from the group comprising Lloyd's mirror, Fresnel's mirror, Fresnel biprism and Billet's slit lens.

19. A method according to claim 1 wherein the assay substrate comprises the assay mask, and the apertures comprise the antiligand coated surface.

20. A method for determining the presence and/or concentration of an analyte in a sample, in which the analyte to be determined is capable of being recognized as a ligand by at lest one antiligand, comprising the steps of:
   a) providing an assay substrate, comprising a narrow surface coated with an antiligand capable of binding the analyte, with the proviso that the coated surface of the assay substrate and areas immediately adjacent to the coated surface are substantially transparent prior to the assay procedure;
   b) reacting the sample with the assay substrate under conditions sufficient to cause the analyte whose presence or concentration is to be determined, if and when present in the sample to bind to the surface coated with the antiligand;
   c) reacting the surface form step b) with an antiligand specific for the analyte immobilized thereon under conditions sufficient to cause the introduced antiligand to bind to the surface substantially only if an when analyte is bound to the surface;
   d) providing an opaque mask containing a transparent slit whose width exceeds the width of the antiligand coated surface on the assay substrate, through which light may be projected to form an interference pattern;
   e) determining the interference pattern formed when light is projected through a slit substantially identical to the slit of the mask provided in step d);
   f) positioning the assay substrate so that its antiligand coated surface lies medially over the center of the slit of the mask provided in step 3);
   g) determining the interference pattern formed when light is projected through the covered slit after the positioning of the surface in steps f); and
   h) correlating changes in one or more features of the interference patterns of steps e) and g) with the presence and/or concentration of the analyte in the sample.

21. A method according to claim 20 wherein the assay substrate comprises the opaque mask, and the apertures comprise the antiligand coated surfaces.

22. The method of claim 20 including further treating the surface from step c), so that at least one optical characteristic of the surface is altered substantially only if, when, and where the antiligand introduced in step c) is bound to the surface.

* * * * *

UNITED STATES PATENT AND TRADEMARK OFFICE
CERTIFICATE OF CORRECTION

PATENT NO. : 5,196,350
DATED : Mar. 23, 1993
INVENTOR(S) : Keith C. Backman and Christiane Munkholm It is certified that error appears in the above-identified patent and that said Letters Patent is hereby corrected as shown below:

Col. 24, line 12, after "sample" insert --,--.
Col. 24, line 14, delete "form" and insert --from--.
Col. 24, line 29, delete "3)" and insert --e)--.
Col. 24, line 32, delete "steps" and insert --step--.

Signed and Sealed this

Seventh Day of December, 1993

Attest:

BRUCE LEHMAN

Attesting Officer

Commissioner of Patents and Trademarks